(12) United States Patent
Inoue et al.

(10) Patent No.: US 11,104,667 B2
(45) Date of Patent: Aug. 31, 2021

(54) METHOD FOR PRODUCING INDOLE COMPOUND

(71) Applicant: JAPAN TOBACCO INC., Tokyo (JP)

(72) Inventors: Teruhiko Inoue, Takatsuki (JP); Koji Matsumura, Takatsuki (JP); Shinichi Kikuchi, Takatsuki (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 16/263,881

(22) Filed: Jan. 31, 2019

(65) Prior Publication Data

US 2019/0161475 A1 May 30, 2019

Related U.S. Application Data

(63) Continuation of application No. 15/323,851, filed as application No. PCT/JP2015/069223 on Jul. 3, 2015, now abandoned.

(30) Foreign Application Priority Data

Jul. 4, 2014 (JP) .................... 2014-138654

(51) Int. Cl.
| | | |
|---|---|---|
| *C07D 403/04* | (2006.01) | |
| *C07D 405/14* | (2006.01) | |
| *C07C 269/00* | (2006.01) | |
| *C07C 271/28* | (2006.01) | |
| *C07D 231/56* | (2006.01) | |
| *C07D 405/04* | (2006.01) | |
| *A61K 31/5377* | (2006.01) | |

(52) U.S. Cl.
CPC .......... *C07D 403/04* (2013.01); *C07C 269/00* (2013.01); *C07C 271/28* (2013.01); *C07D 231/56* (2013.01); *C07D 405/04* (2013.01); *C07D 405/14* (2013.01); *A61K 31/5377* (2013.01)

(58) Field of Classification Search
CPC .................................................. C07D 403/04
See application file for complete search history.

(56) References Cited

U.S. PATENT DOCUMENTS

| | | |
|---|---|---|
| 8,778,984 B2 | 7/2014 | Bell et al. |
| 9,174,968 B2 | 11/2015 | Jin et al. |
| 2011/0306599 A1 | 12/2011 | Inoue et al. |
| 2012/0142717 A1 | 6/2012 | Jin et al. |
| 2013/0116240 A1 | 5/2013 | Inoue et al. |
| 2013/0252963 A1 | 9/2013 | Jin et al. |
| 2014/0113922 A1 | 4/2014 | Jin et al. |
| 2015/0099756 A1 | 4/2015 | Jin et al. |
| 2017/0253577 A1 | 9/2017 | Inoue et al. |
| 2017/0267662 A1 | 9/2017 | Inoue et al. |
| 2018/0362506 A1 | 12/2018 | Inoue et al. |
| 2020/0255408 A1 | 8/2020 | Inoue et al. |

FOREIGN PATENT DOCUMENTS

| | | |
|---|---|---|
| JP | 2011-132222 A | 7/2011 |
| JP | 2013-544860 A | 12/2013 |
| WO | WO 2011/065402 A1 | 6/2011 |
| WO | WO 2012/173849 A1 | 12/2012 |

OTHER PUBLICATIONS

Bonjoch et al., "Synthesis of 2-(4-piperidylmethyl)indoles. Intermediates for the Synthesis of Strychnos Alkaloids," *Heterocycles*, 27(12): 2883-2890 (1988).
Bunce et al., "1,2,3,9-Tetrahydro-4H-carbazol-4-one and 8,9-Dihydropyrido-[1,2-α] indol-6(7H)-one from 1H-Indole-2-butanoic Acid," *J. Heterocyclic Chem.*, 46(2): 172-177 (2009).
The Chemical Society of Japan, "Dai 4 Ban Jikken Kagaku Koza 1 Kihon Sosa I," *Experimental Chemistry Course 1, Basic Operations I*, Fourth Edition, pp. 184-186 (1990).
Wang et al., "Substituent Diversity-Directed Synthesis of Indole Derivatives," *J. Comb. Chem.*, 11(4): 556-575 (2009).
Japanese Patent Office, International Search Report in International Patent Application No. PCT/JP2015/069223 (dated Sep. 29, 2015).

(Continued)

*Primary Examiner* — Paul V Ward
(74) *Attorney, Agent, or Firm* — Leydig, Voit & Mayer, Ltd.

(57) ABSTRACT

The present invention aims to provide a new method for producing an indole compound or a salt thereof, which has an ITK inhibitory action, and is useful for the prophylaxis or treatment of inflammatory disease.

The present invention is a method for producing N-[2-(6,6-dimethyl-4,5,6,7-tetrahydro-1H-indazol-3-yl)-1H-indol-6-yl]-N-methyl-(2S)-2-(morpholin-4-yl)propanamide, which comprises a step of reacting

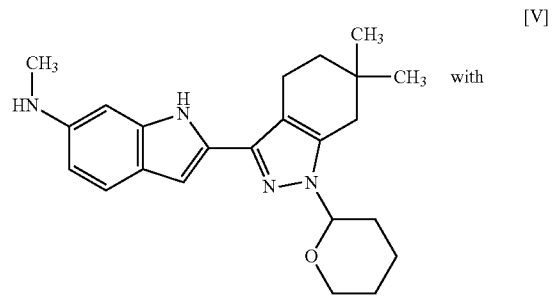

with

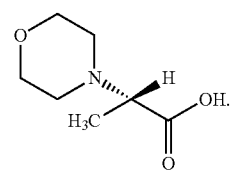

8 Claims, 1 Drawing Sheet

(56) References Cited

OTHER PUBLICATIONS

Japanese Patent Office, Written Opinion of the International Searching Authority in International Patent Application No. PCT/JP2015/069223 (dated Sep. 29, 2015).
U.S. Appl. No. 15/323,851, filed May 15, 2017.
U.S. Appl. No. 17/029,642, filed Sep. 23, 2020, Inoue et al.

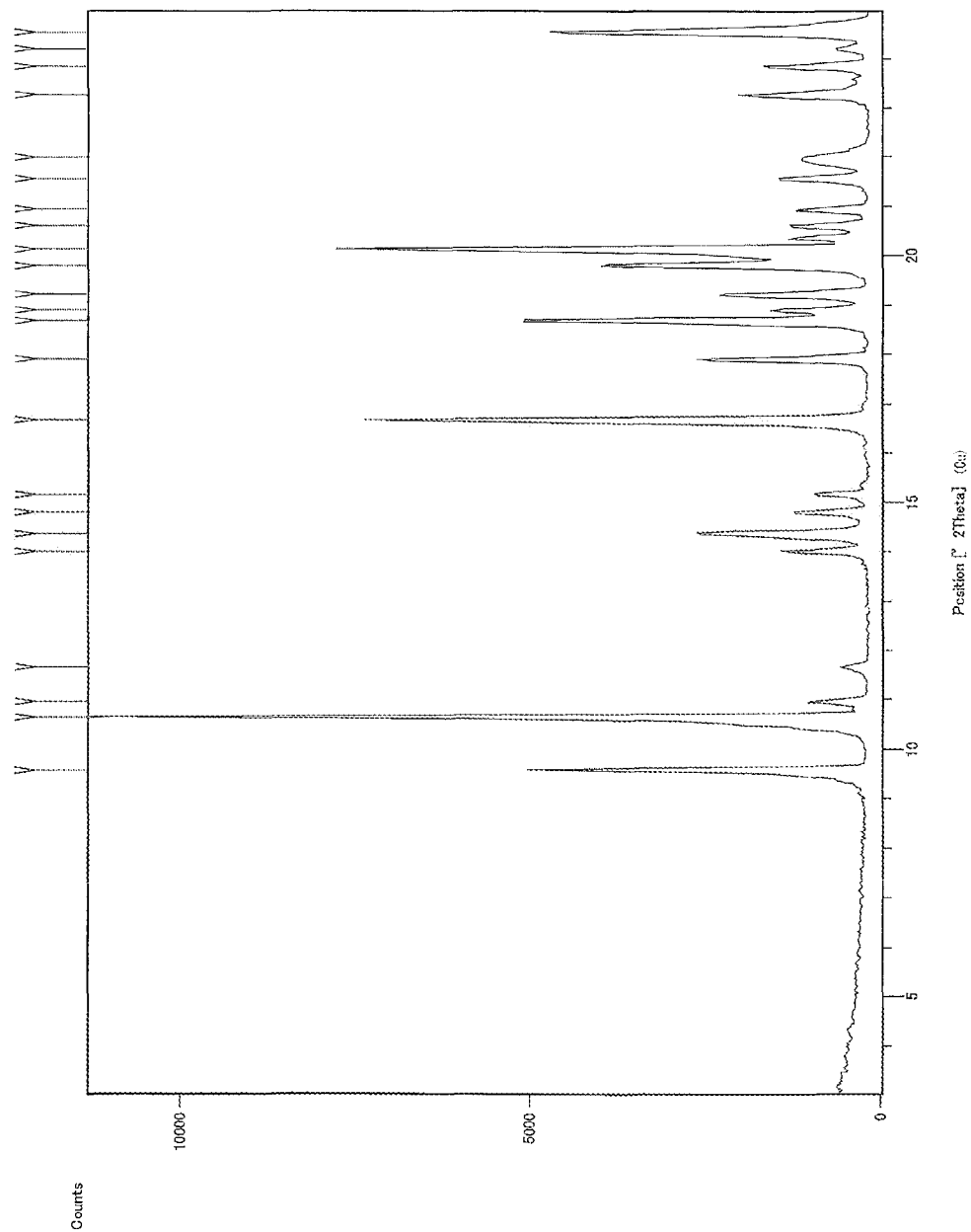

METHOD FOR PRODUCING INDOLE COMPOUND

TECHNICAL FIELD

The present invention relates to a new method for producing an indole compound or a salt thereof, which is useful as an inducible T cell kinase (ITK) inhibitor, and an intermediate thereof.

BACKGROUND ART

Patent Document 1 discloses a compound useful as an ITK inhibitor, and a method for producing the same.

DOCUMENT LIST

Patent Document

Patent Document 1: WO 2011/065402

SUMMARY OF THE INVENTION

The present invention aims to provide a new method for producing an indole compound or a salt thereof, which is useful for the prophylaxis or treatment of inflammatory disease, and the like.

Embodiments of the present invention are shown in the following (1) to (16).

(1) A method of producing N-[2-(6,6-dimethyl-4,5,6,7-tetrahydro-1H-indazol-3-yl)-1H-indol-6-yl]-N-methyl-(2S)-2-(morpholin-4-yl)propanamide (formula [I]

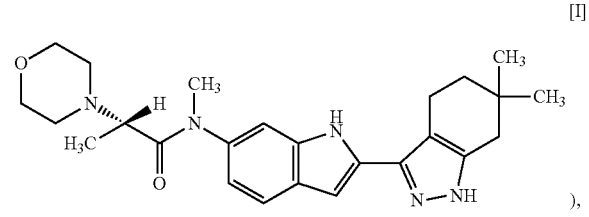 [SMILES: C[C@@H](C(=O)N(C)c1ccc2cc(-c3n[nH]c4c3CCC(C)(C)C4)[nH]c2c1)N1CCOCC1]

which comprises a step of removing the protecting group from N-[2-(6,6-dimethyl-1-(tetrahydropyran-2-yl)-4,5,6,7-tetrahydro-1H-indazol-3-yl)-1H-indol-6-yl]-N-methyl-(2S)-2-(morpholin-4-yl)propanamide (formula [III]

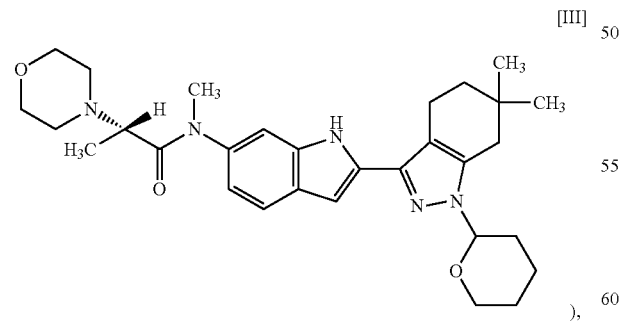

to give a compound of the formula [I].

(2) A method of producing N-[2-(6,6-dimethyl-4,5,6,7-tetrahydro-1H-indazol-3-yl)-1H-indol-6-yl]-N-methyl-(2S)-2-(morpholin-4-yl)propanamide monohydrochloride (formula [II]

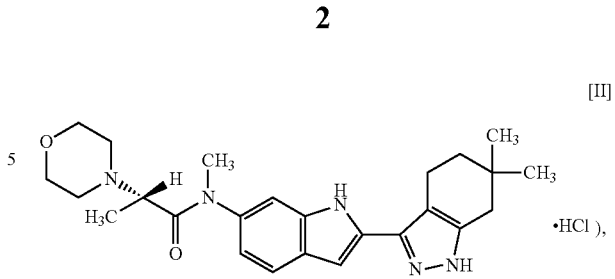

which comprises a step of reacting N-[2-(6,6-dimethyl-4,5,6,7-tetrahydro-1H-indazol-3-yl)-1H-indol-6-yl]-N-methyl-(2S)-2-(morpholin-4-yl)propanamide (formula [I]

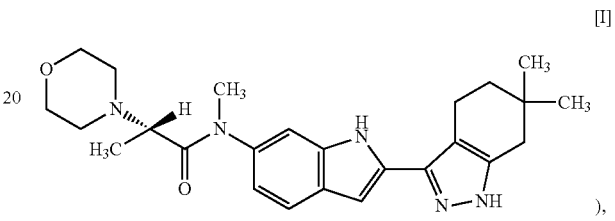

with hydrogen chloride to give a compound of the formula [II].

(3) A method of producing N-[2-(6,6-dimethyl-4,5,6,7-tetrahydro-1H-indazol-3-yl)-1H-indol-6-yl]-N-methyl-(2S)-2-(morpholin-4-yl)propanamide monohydrochloride (formula [II]

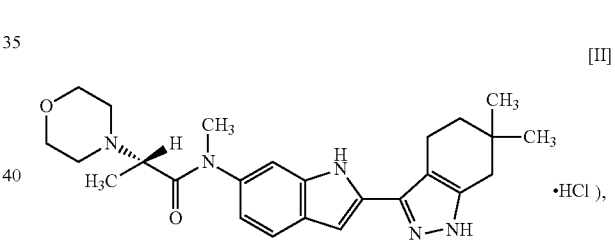

which comprises a step of removing the protecting group from N-[2-(6,6-dimethyl-1-(tetrahydropyran-2-yl)-4,5,6,7-tetrahydro-1H-indazol-3-yl)-1H-indol-6-yl]-N-methyl-(2S)-2-(morpholin-4-yl)propanamide (formula [III]

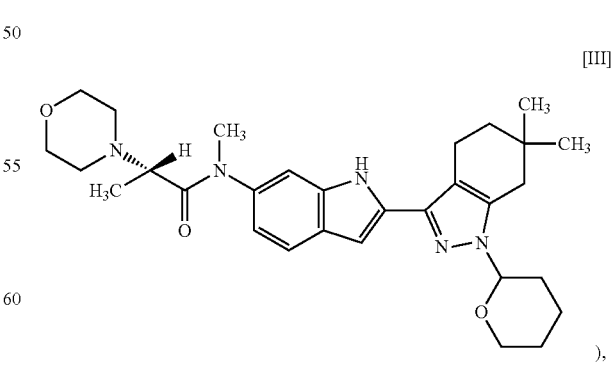

to give N-[2-(6,6-dimethyl-4,5,6,7-tetrahydro-1H-indazol-3-yl)-1H-indol-6-yl]-N-methyl-(2S)-2-(morpholin-4-yl)propanamide (formula [I]

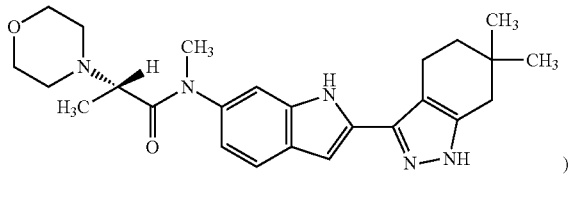

and a step of treating a compound of the formula [I] with hydrogen chloride to give a compound of the formula [II].

(4) The method of (1) or (3), which further comprises a step of reacting N-[2-[6,6-dimethyl-1-(tetrahydropyran-2-yl)-4,5,6,7-tetrahydro-1H-indazol-3-yl]-1H-indol-6-yl]-N-methylamine (formula [V]

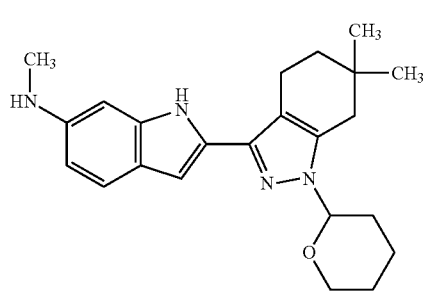

with (2S)-2-(morpholin-4-yl)propanoic acid (formula [IV]

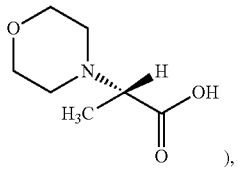

or reactive derivative thereof or a salt thereof to give N-[2-(6,6-dimethyl-1-(tetrahydropyran-2-yl)-4,5,6,7-tetrahydro-1H-indazol-3-yl]-1H-indol-6-yl]-N-methyl-(2S)-2-(morpholin-4-yl)propanamide (formula [III]

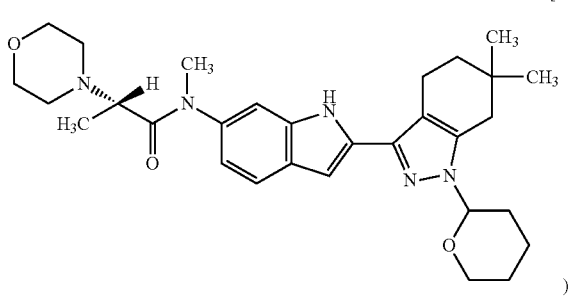

(5) The method of (4), which further comprises a step of subjecting a compound of the formula [VI]

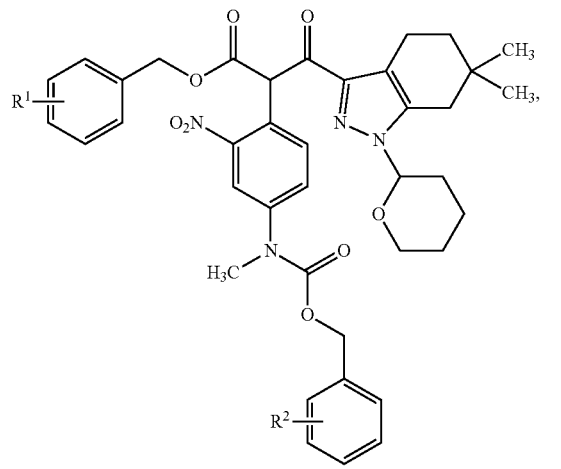

wherein $R^1$ and $R^2$ are each independently hydrogen, $C_{1-6}$ alkyl or $C_{1-6}$ alkoxy, to a reduction reaction to give N-[2-[6,6-dimethyl-1-(tetrahydropyran-2-yl)-4,5,6,7-tetrahydro-1H-indazol-3-yl]-1H-indol-6-yl]-N-methylamine (formula [V]

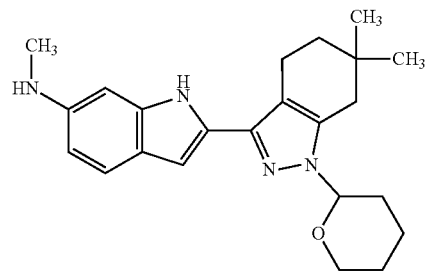

(6) The method of (5), which further comprises a step of reacting a compound of the formula [VII]

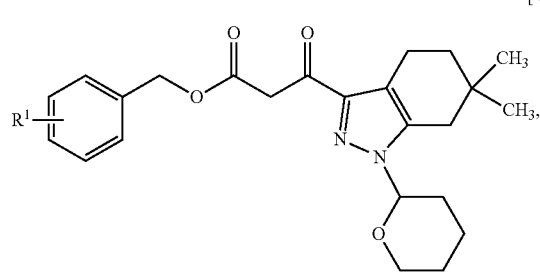

wherein $R^2$ is as defined above, with a compound of the formula [XI]

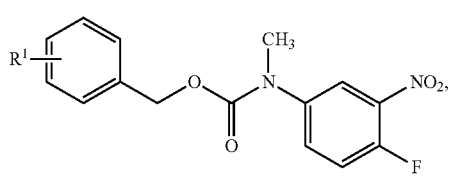
[XI]

wherein R² is as defined above,
to give a compound of the formula [VI]

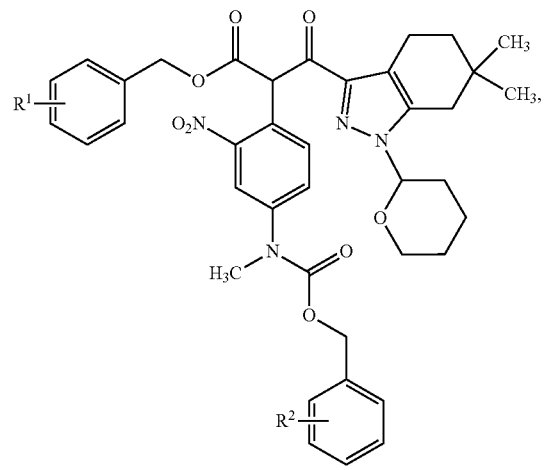
[VI]

wherein R¹ and R² are as defined above.

(7) The method of (6), which further comprises a step of subjecting a compound of the formula [VIII]

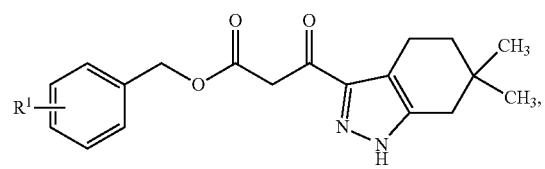
[VIII]

wherein R¹ is as defined above,
to tetrahydropyranylation to give a compound of the formula [VII]

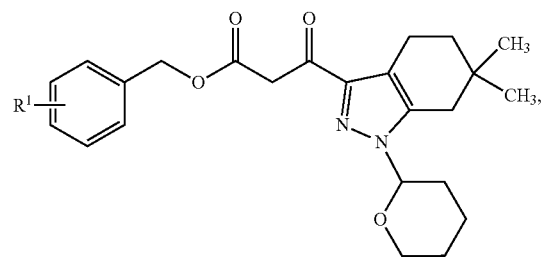
[VII]

wherein R¹ is as defined above.

(8) The method of (7), which further comprises a step of reacting 6,6-dimethyl-4,5,6,7-tetrahydro-1H-indazole-3-carboxylic acid (formula [IX]

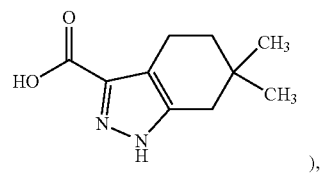
[IX]

with a compound of the formula [X]

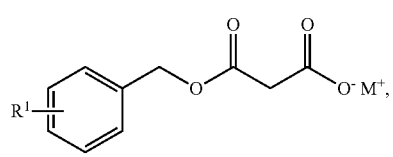
[X]

wherein
M is sodium or potassium, and
R¹ is as defined above,
to give a compound of the formula [VIII]

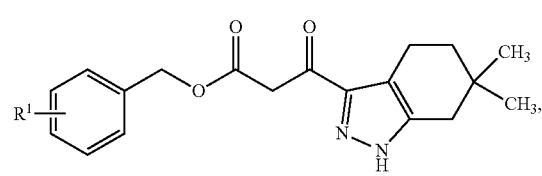
[VIII]

wherein R¹ is as defined above.

(9) The method of (2) or (3), which further comprises a step of purifying N-[2-(6,6-dimethyl-4,5,6,7-tetrahydro-1H-indazol-3-yl)-1H-indol-6-yl]-N-methyl-(2S)-2-(morpholin-4-yl)propanamide monohydrochloride (formula [II]

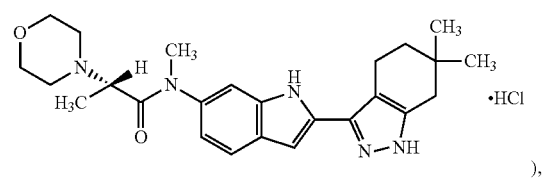
[II]

with 1-propanol.

(10) A method of producing a compound of the formula [XI]

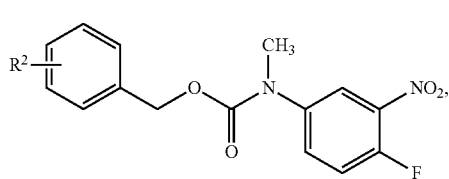
[XI]

wherein R² is as defined above,
which comprises a step of subjecting a compound of the formula [XII]

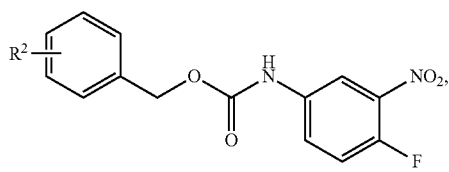
[XII]

wherein R² is as defined above,
to methylation.

(11) N-[2-[6,6-dimethyl-1-(tetrahydropyran-2-yl)-4,5,6,7-tetrahydro-1H-indazol-3-yl]-1H-indol-6-yl]-N-methyl-amine (formula [V])

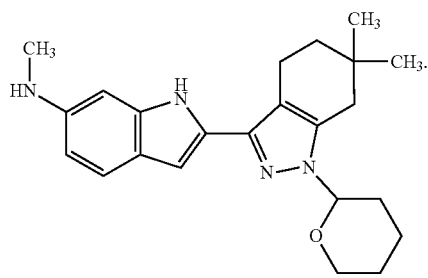
[V]

(12) N-[2-(6,6-dimethyl-1-(tetrahydropyran-2-yl)-4,5,6,7-tetrahydro-1H-indazol-3-yl]-1H-indol-6-yl]-N-methyl-(2S)-2-(morpholin-4-yl)propanamide (formula [III])

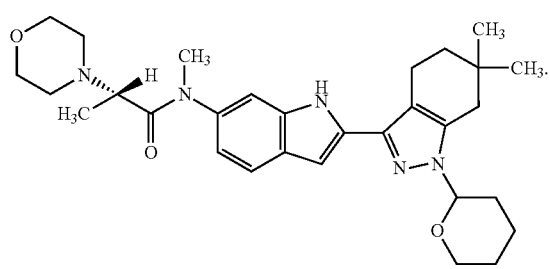
[III]

(13) A compound of the formula [VI]

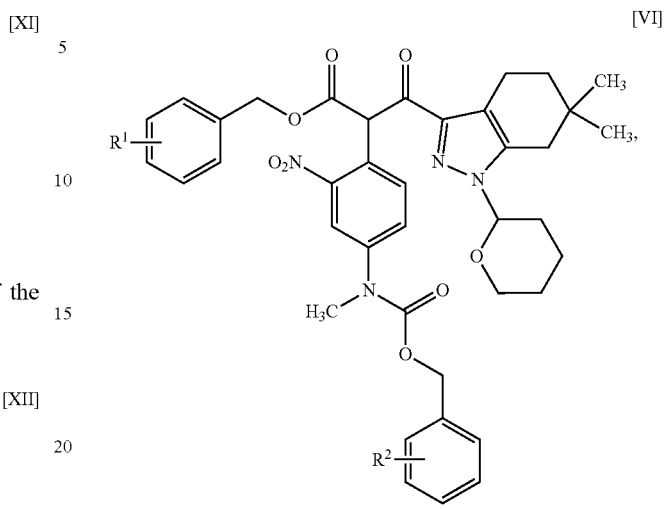
[VI]

wherein R¹ and R² are as defined above.

(14) A compound of the formula [VII]

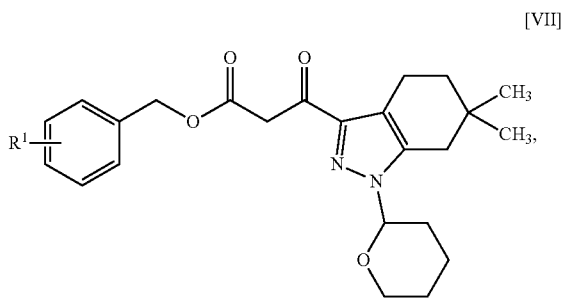
[VII]

wherein R² is as defined above.

(15) A compound of the formula [VIII]

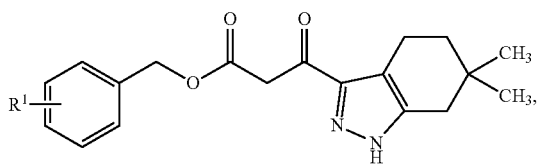
[VIII]

wherein R² is as defined above.

(16) A compound of the formula [XI]

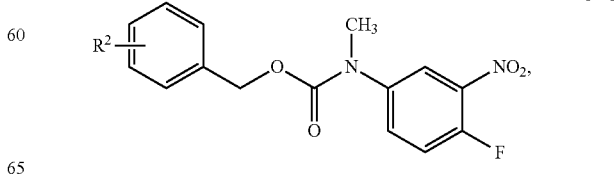
[XI]

wherein R² is as defined above.

Effect of the Invention

According to the production method of the present invention, an indole compound having an ITK inhibitory action, which is useful for the prophylaxis or treatment of inflammatory disease, and the like, can be produced via compound considered to be free from safety concerns, in a few steps and in good yield. In addition, a new intermediate for producing the indole compound can also be provided by the method.

BRIEF DESCRIPTION OF THE DRAWINGS

FIG. 1 shows multi record of powder X-ray diffraction pattern of N-[2-[6,6-dimethyl-1-(tetrahydropyran-2-yl)-4,5,6,7-tetrahydro-1H-indazol-3-yl]-1H-indol-6-yl]-N-methylamine. The axis of ordinate shows diffraction strength (cps: counts per second), and the axis of abscissas shows diffraction angle 2θ(°).

EMBODIMENTS OF THE INVENTION

The definitions of the terms used in the present specification are as follows.

The "$C_{1-6}$ alkyl" means straight chain or branched chain alkyl having 1 to 6 carbon atoms, preferably straight chain or branched chain alkyl having 1 to 4 carbon atoms. Examples thereof include methyl, ethyl, propyl, isopropyl, butyl, isobutyl, sec-butyl, tert-butyl, pentyl, isopentyl, tert-pentyl, 1-ethylpropyl, neo-pentyl, hexyl, 2-ethylbutyl, 3,3-dimethylbutyl and the like. Methyl, ethyl, propyl, isopropyl, butyl, isobutyl, sec-butyl and tert-butyl are preferable, and methyl is particularly preferable.

The "$C_{1-6}$ alkoxy" means alkyl-oxy wherein the alkyl moiety is the above-defined "$C_{1-6}$ alkyl". Examples thereof include methoxy, ethoxy, propoxy, isopropoxy, butoxy, isobutoxy, sec-butoxy, tert-butoxy, pentoxy, isopentoxy, tert-pentoxy, 1-ethylpropoxy, neopentoxy, hexoxy, 2-ethylbutoxy, 3,3-dimethylbutoxy and the like. Methoxy, ethoxy, propoxy, isopropoxy, butoxy, isobutoxy, sec-butoxy and tert-butoxy are preferable, and methoxy is particularly preferable.

Compounds [III], [V], [VI] and [VII] of the present invention have tetrahydropyranyl as a protecting group at the 1-position on the 4,5,6,7-tetrahydro-1H-indazole moiety. The compounds may have methoxymethyl instead of tetrahydropyranyl.

The protecting group at the 1-position on the 4,5,6,7-tetrahydro-1H-indazole moiety in the compound of the present invention is preferably tetrahydropyranyl.

The "reactive derivative" of the carboxylic acid may be any carboxylic acid derivative as long as it can form an amide bond. Examples thereof include acid halides, anhydrides and the like. Acid halides are preferable.

The "salt" of the compound may be any salt as long as it forms a salt with the compound of the present invention. Examples thereof include salts with inorganic acid, salts with organic acid, salts with inorganic base, salts with organic base, salts with amino acid, and the like.

Examples of the salts with inorganic acid include salts with hydrochloric acid, nitric acid, sulfuric acid, phosphoric acid, hydrobromic acid and the like.

Examples of the salts with organic acid include salts with oxalic acid, maleic acid, citric acid, fumaric acid, lactic acid, malic acid, succinic acid, tartaric acid, acetic acid, trifluoroacetic acid, gluconic acid, ascorbic acid, methanesulfonic acid, benzenesulfonic acid, p-toluenesulfonic acid and the like.

Examples of the salts with inorganic base include sodium salt, potassium salt, calcium salt, magnesium salt, ammonium salt and the like.

Examples of the salts with organic base include salts with methylamine, diethylamine, trimethylamine, triethylamine, ethanolamine, diethanolamine, triethanolamine, ethylenediamine, tris(hydroxymethyl)methylamine, dicyclohexylamine, N,N'-dibenzylethylenediamine, guanidine, pyridine, picoline, choline, cinchonine, meglumine and the like.

Examples of the salts with amino acid include salts with lysine, arginine, aspartic acid, glutamic acid and the like.

The salt of compound [IV] is preferably hydrochloride, particularly preferably monohydrochloride.

The "halogen" means fluorine, chlorine, bromine, iodine or the like. Chlorine and bromine are preferable, and chlorine is particularly preferable.

The "methylating agent" means a reagent capable of introducing methyl into a reactive functional group such as —NH— and the like. Examples thereof include methyl iodide, dimethylsulfuric acid and the like. Methyl iodide is preferable.

The formula [VI]

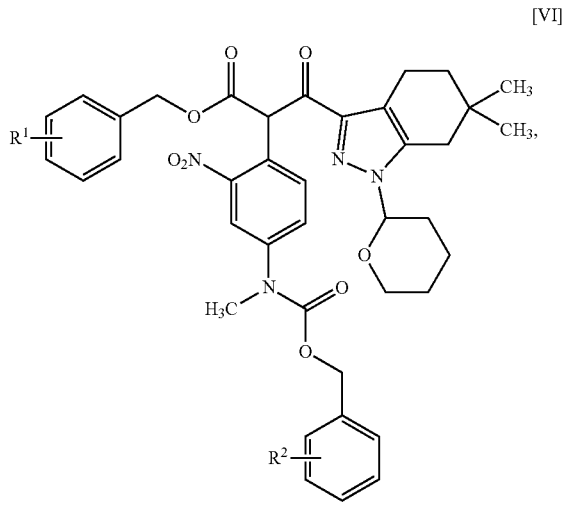

[VI]

wherein $R^1$ and $R^2$ are each independently hydrogen, $C_{1-6}$ alkyl or $C_{1-6}$ alkoxy,
is preferably the formula [VI-1] (benzyl 2-[4-(N-benzyloxycarbonyl-N-methylamino)-2-nitrophenyl]-3-[6,6-dimethyl-1-(tetrahydropyran-2-yl)-4,5,6,7-tetrahydro-1H-indazol-3-yl]-3-oxopropanoate)

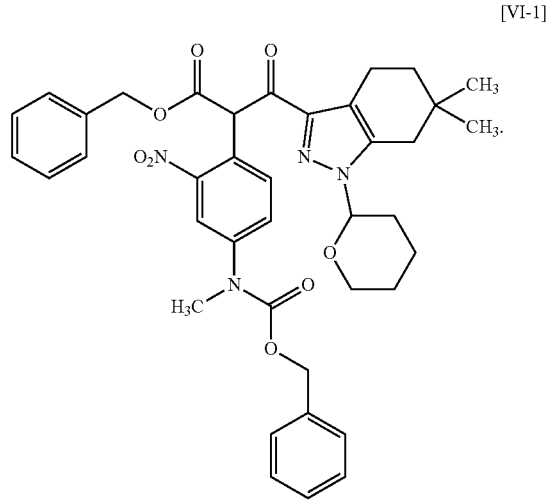 [SMILES: CN(C(=O)OCc1ccccc1)c1ccc(C(C(=O)OCc2ccccc2)C(=O)c2nn(C3CCCCO3)c3c2CCC(C)(C)C3)c([N+](=O)[O-])c1]

[VI-1]

The formula [VII]

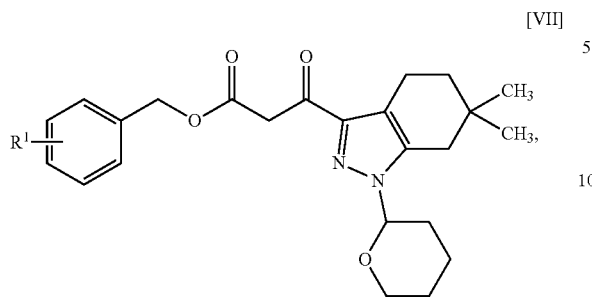

wherein R¹ is as defined above, is preferably formula [VII-1] (benzyl 3-[6,6-dimethyl-1-(tetrahydropyran-2-yl)-4,5,6,7-tetrahydro-1H-indazol-3-yl]-3-oxopropanoate)

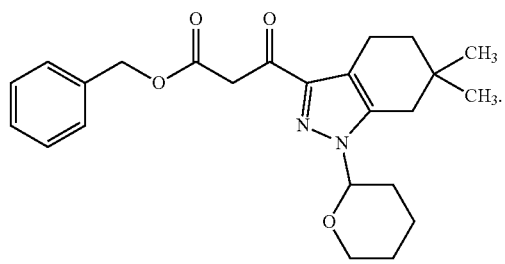

The formula [VIII]

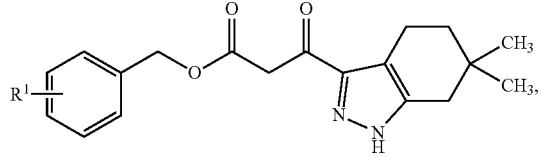

wherein R¹ is as defined above, is preferably formula [VIII-1] (benzyl 3-(6,6-dimethyl-4,5,6,7-tetrahydro-1H-indazol-3-yl)-3-oxopropanoate)

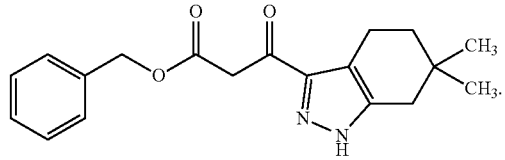

The formula [X]

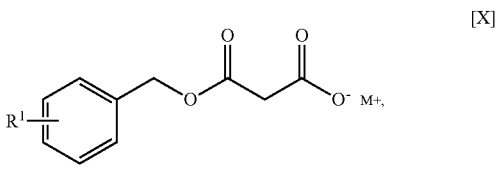

wherein M is sodium or potassium, R¹ is as defined above, is preferably formula [X-1] (monobenzyl potassium malonate)

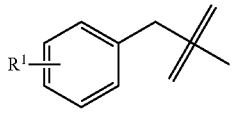

The moiety

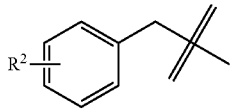

in the above-mentioned compounds [VI], [VII], [VIII] and [X], and the moiety

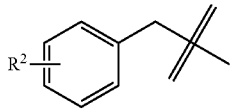

in the above-mentioned compounds [VI], [XI] and [XII] and the below-mentioned compound [XIV] are carboxy-protecting groups, preferably benzyl (R² is hydrogen). The moieties can be each replaced by another moiety. Examples of such moiety include 4-methoxybenzyl (R² is methoxy) and 4-methylbenzyl (R² is methyl).

The compound of the present invention may exist as a tautomer. In this case, the compound of the present invention may exist as a single tautomer or a mixture thereof.

The compound of the present invention may contain one or more asymmetric carbons. In this case, the compound of the present invention may exist as a single enantiomer, a single diastereomer, a mixture of enantiomers or a mixture of diastereomers.

The compound of the present invention may exist as an atropisomer. In this case, the compound of the present invention may exist as a single atropisomer or a mixture thereof.

The compound of the present invention may simultaneously contain plural structural characteristics that produce the above-mentioned isomers. Moreover, the compound of the present invention may contain the above-mentioned isomers at any ratio.

Unless otherwise referred to note, the formulae, chemical structures and compound names indicated in the present specification without specifying the stereochemistry thereof encompass all the above-mentioned isomers that may exist.

A diastereomeric mixture can be separated into each diastereomer by a conventional method such as chromatography, crystallization and the like. In addition, each diastereomer can also be produced by using a stereochemically single starting material, or by a synthetic method employing a stereoselective reaction.

An enantiomeric mixture can be separated into each single enantiomer by a method well known in the art.

For example, a diastereomic mixture can be prepared by reacting an enantiomeric mixture with a substantially pure enantiomer that is known as a chiral auxiliary, and the diastereomeric mixture can be separated into single diastereomer having a high isomer ratio or substantially pure single diastereomer by a standard method such as fractional crystallization and chromatography. The separated diastereomer can be converted to a desired enantiomer by removing the added chiral auxiliary by cleavage.

In addition, an enantiomeric mixture can also be directly separated by a chromatography method using a chiral solid phase well known in the art.

Alternatively, one of enantiomers can also be obtained by using a substantially pure optically active starting material or by employing stereoselective synthesis (asymmetric induction) of a prochiral intermediate using a chiral auxiliary and an asymmetric catalyst.

The absolute steric configuration can be determined based on the X-ray crystal analysis of the crystalline product or intermediate. In this case, a crystalline product or intermediate derivatized with a reagent having an asymmetric center with a known steric configuration may be used if necessary.

The production method of the present invention is concretely explained in the following.

In each step, the treatment after reaction can be performed by a general method, and the product can be purified by appropriately selecting or combining a conventional method such as distillation, crystallization, recrystallization, column chromatography, preparative HPLC, slurry washing and the like. The product may be directly used in the next step without isolation or purification.

Step 1

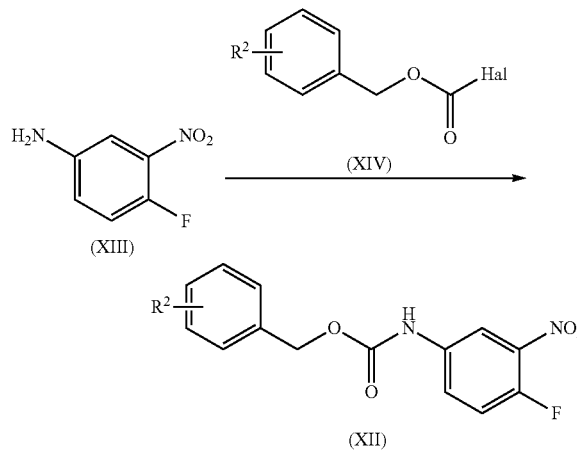

wherein $R^2$ is hydrogen, $C_{1-6}$ alkyl or $C_{1-6}$ alkoxy, and Hal is halogen.

Compound [XII] can be obtained by reacting 4-fluoro-3-nitroaniline (compound [XIII]) with compound [XIV] in an ester solvent (ethyl acetate, etc.), an ether solvent (tetrahydrofuran, dimethyl ether, diethyl ether, etc.), a polar solvent (dimethyl sulfoxide, N,N-dimethylformamide, etc.) or the like or in a mixed solvent thereof, in the presence of an inorganic base (sodium hydrogencarbonate, potassium hydrogencarbonate, sodium carbonate, potassium carbonate) or an organic base (triethylamine, N,N-diisopropylethylamine, pyridine, etc.). When an inorganic base is used, water may be mixed with an inorganic base. The amount of compound [XIV] is 1.05 equivalent to 1.5 equivalent, preferably 1.1 equivalent, relative to 4-fluoro-3-nitroaniline. The amount of the base is 1.5 equivalent to 1.1 equivalent, preferably 1.3 equivalent, relative to 4-fluoro-3-nitroaniline. The reaction temperature is 0° C. to 50° C., preferably room temperature. The reaction time is 1 hr to 10 hr, preferably 2 hr to 4 hr, particularly preferably 3 hr.

Compound [XIV] may be a commercially available product, or can be prepared by a known method from a benzyl alcohol having a desired substituent and a carbonyldihalogen such as phosgene and the like.

Step 2

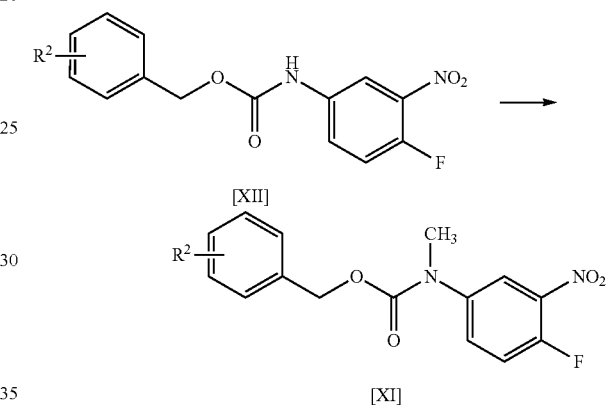

wherein $R^2$ is as defined above.

Compound [XI] can be obtained by reacting compound [XII] with a methylating agent such as methyl iodide, dimethylsulfuric acid and the like, in a solvent such as a polar solvent (dimethyl sulfoxide, N,N-dimethylformamide, N,N-dimethylacetamide, etc.), an ether solvent (tetrahydrofuran, dimethyl ether, diethyl ether, etc.) and the like, in the presence of an inorganic base (cesium carbonate, sodium carbonate, potassium carbonate, sodium hydrogencarbonate, potassium hydrogencarbonate, sodium hydride, sodium tert-butoxide, etc.). The amount of the methylating agent is 1.1 equivalent to 1.5 equivalent, preferably 1.2 equivalent, relative to compound [XII]. The amount of the inorganic base is 1.1 equivalent to 1.5 equivalent, preferably 1.2 equivalent, relative to compound [XII]. The reaction temperature is 0° C. to 40° C., preferably 20° C. to 10° C. The reaction time is 1 hr to 10 hr, preferably 2 hr to 4 hr, particularly preferably 3 hr.

Step 3

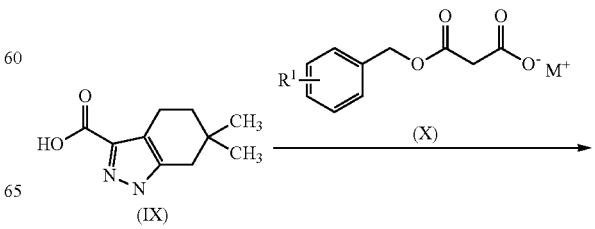

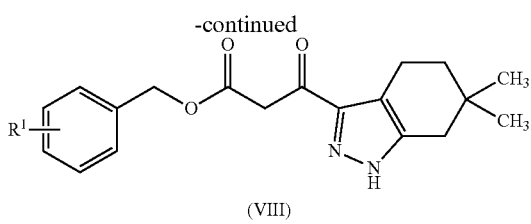

(VIII)

wherein $R^1$ is hydrogen, $C_{1-6}$ alkyl or $C_{1-6}$ alkoxy, and M is sodium or potassium.

(1) 6,6-Dimethyl-4,5,6,7-tetrahydro-1H-indazole-3-carboxylic acid (compound [IX]) is reacted with a condensing agent such as 1,1'-carbonyldiimidazole, 1-ethyl-3-(3-dimethylaminopropyl)carbodiimide, dicyclohexylcarbodiimide and the like, in a polar solvent (dimethyl sulfoxide, N,N-dimethylformamide, etc.), an aromatic hydrocarbon (benzene, toluene, etc.), an ether solvent (tetrahydrofuran, dimethyl ether, diethyl ether, etc.) or the like or in a mixed solvent thereof, for 1 hr to 3 hr, preferably for 2 hr or more.

(2) Separately, compound [X] is reacted with magnesium chloride in a polar solvent (dimethyl sulfoxide, N,N-dimethylformamide, etc.), an aromatic hydrocarbon (benzene, toluene, etc.), an ether solvent (tetrahydrofuran, dimethyl ether, diethyl ether, etc.) or the like or in a mixed solvent thereof, and the resulting product is mixed with the mixture obtained in (1), and the mixture is reacted for 1 hr to 3 hr, preferably for 3 hr, to give compound [VIII]. In this reaction, the reaction rate can be increased and the yield can be improved, by addition of a tertiary amine (triethylamine, diisopropylethylamine, etc.). To improve the yield, the amount of compound [X] is 1.5 equivalent or more, preferably 2 equivalent, relative to compound [IX]. The amount of the condensing agent is 1.0 equivalent to 1.5 equivalent, preferably 1.1 equivalent, relative to compound [IX]. The amount of the magnesium chloride is 1.1 equivalent to 1.5 equivalent, preferably 1.25 equivalent, relative to compound [X]. When a tertiary amine is added, solvent amount thereof may be added 2 hr after reaction initiation, or later. The reaction temperature is 0° C. to 100° C., preferably 45° C. to 55° C. The reaction mixture is preferably warmed to 65° C. to 75° C. depending on the reaction progress. The reaction time is 1 hr to 10 hr, preferably 2 hr to 6 hr.

Compound [X] may be a commercially available product, or can be prepared by a known method from a benzyl alcohol having a desired substituent and malonic acid.

Step 4

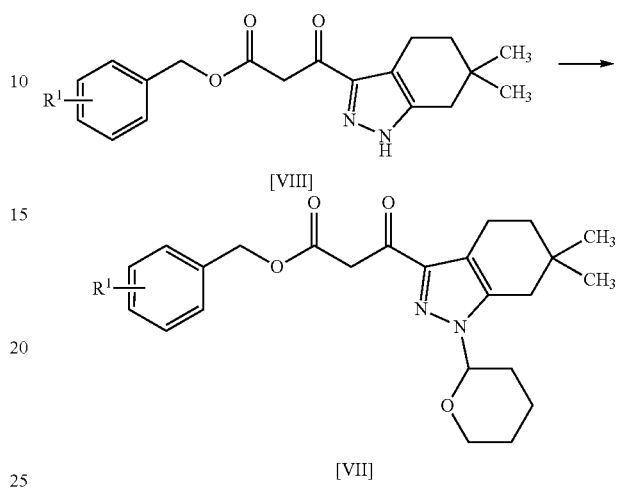

wherein $R^1$ is as defined above.

Compound [VII] can be obtained by reacting compound [VIII] with 3,4-dihydro-2H-pyran in a solvent such as an ester solvent (ethyl acetate, etc.), a polar solvent (N,N-dimethylformamide, etc.), an ether solvent (tetrahydrofuran, etc.), an aromatic hydrocarbon (toluene, etc.) and the like, in the presence of an organic acid (p-toluenesulfonic acid, methanesulfonic acid, etc.). The amount of the 3,4-dihydro-2H-pyran is 1.1 equivalent to 2 equivalent, preferably 1.5 equivalent, relative to compound [VIII]. The amount of the organic acid is a catalyst amount (for example 0.05 equivalent). The reaction temperature is 0° C. to 50° C., preferably 15° C. to 30° C. The reaction temperature is 1 hr to 5 hr, preferably 2 hr. The solvent to be used for this reaction is preferably ethyl acetate, since the production of impurities can be suppressed, compared with N,N-dimethylformamide, tetrahydrofuran or toluene.

While the configuration of the carbon at the 2-position on the tetrahydropyranyl in compound [VII] may contain R and S, compound [VII] can be used in the next step without optical resolution.

Step 5

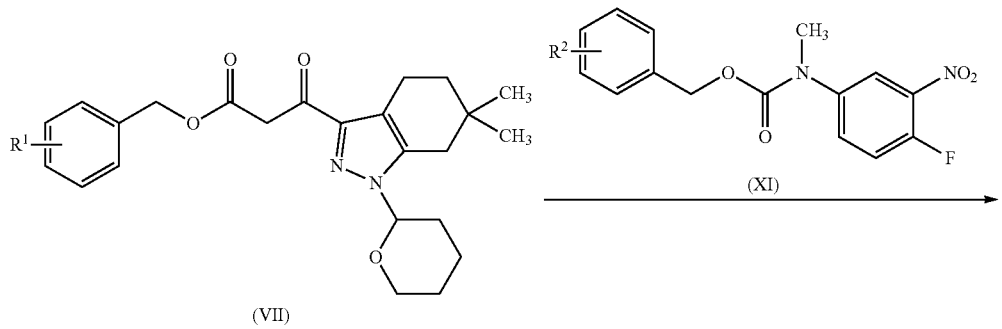

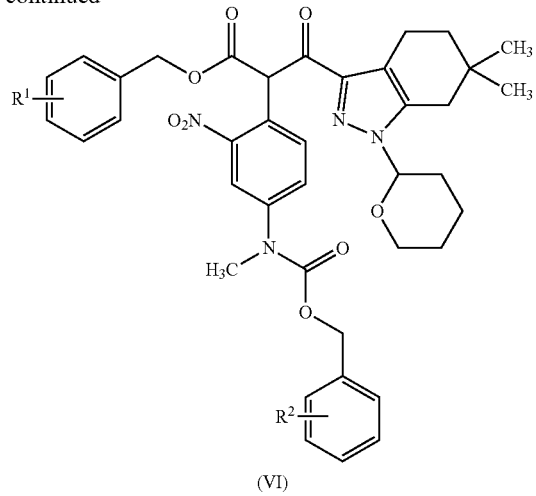

(VI)

wherein R¹ and R² are as defined above.

Compound [VI] can be obtained by reacting compound [VII] with compound [XI] in an ether solvent (tetrahydrofuran, dimethyl ether, diethyl ether, etc.), a polar solvent (dimethyl sulfoxide, N,N-dimethylformamide, N,N-dimethylacetamide, etc.) or a mixed solvent thereof, in the presence of an inorganic base (tripotassium phosphate, cesium carbonate, sodium carbonate, potassium carbonate, etc.). The molar ratio of compound [VII] and compound [XI] is preferably about 1:1. The amount of the inorganic base is 2 equivalent to 3 equivalent, preferably 2.5 equivalent, relative to compound [VII]. The reaction temperature is 30° C. to 100° C., preferably 50° C. to 60° C. The reaction time is 2 hr to 30 hr, preferably 20 hr.

Step 6

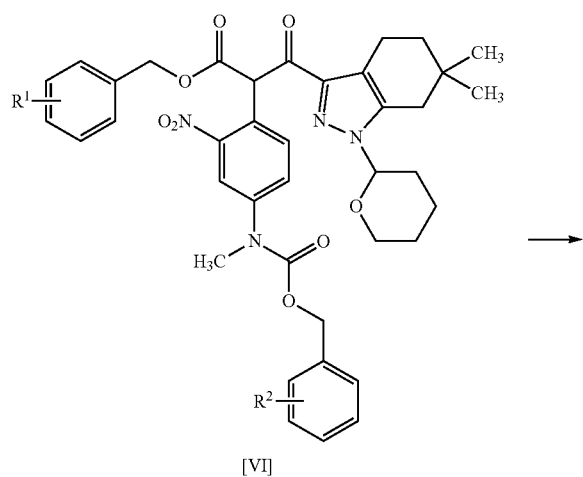

[VI]

→

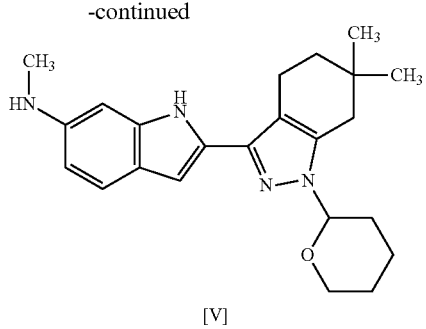

[V]

wherein R¹ and R² are as defined above.

N-[2-[6,6-Dimethyl-1-(tetrahydropyran-2-yl)-4,5,6,7-tetrahydro-1H-indazol-3-yl]-1H-indol-6-yl]-N-methylamine (compound [V]) can be obtained by subjecting compound [VI] to a reduction reaction by hydrogenation in an alcohol (methanol, ethanol, 1-propanol, 2-propanol, etc.) alone, or in a mixed solvent of an alcohol with an aromatic hydrocarbon (toluene, benzene, etc.), an ether solvent (tetrahydrofuran, dimethyl ether, diethyl ether, etc.), an ester solvent (ethyl acetate, etc.) or the like, in the presence of a palladium catalyst (palladium on carbon (preferably PE type), palladium black, palladium hydroxide carbon or the like, preferably palladium on carbon PE type). The hydrogen pressure is 1 atm to 10 atm, preferably 3 atm to 4 atm. The reaction temperature is 0° C. to 50° C., preferably 15° C. to 30° C. The reaction time is 5 hr to 40 hr, preferably 20 hr.

Since compound [V] is crystallized, it can be purified. In particular, the color substance produced in the reaction can be removed. When purification is performed by recrystallization or slurry washing, a mixed solvent of toluene and 2-propanol is preferably used.

Step 7

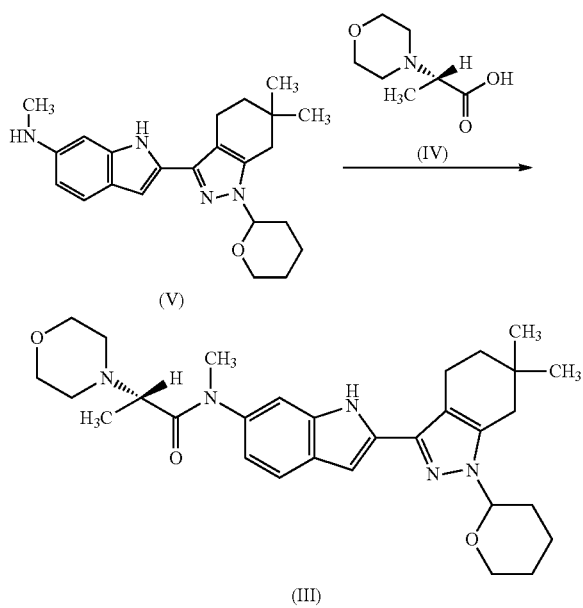

N-[2-(6,6-Dimethyl-1-(tetrahydropyran-2-yl)-4,5,6,7-tetrahydro-1H-indazol-3-yl)-1H-indol-6-yl]-N-methyl-(2S)-2-(morpholin-4-yl)propanamide (compound [III]) can be obtained by reacting compound [V] with (S)-2-(morpholin-4-yl)propanoic acid (compound [IV]) or a salt thereof, using a condensing agent (1-ethyl-3-(3-dimethylaminopropyl)carbodiimide or a salt thereof, dicyclohexylcarbodiimide, diisopropylcarbodiimide, etc.), in the presence of a reaction accelerator (1-hydroxybenzotriazole or a hydrate thereof, etc.), in a solvent such as polar solvent (dimethyl sulfoxide, N,N-dimethylformamide, etc.), an ether solvent (tetrahydrofuran, dimethyl ether, diethyl ether, etc.) and the like. When a salt of compound [IV] is used, a base (sodium hydrogencarbonate, potassium hydrogencarbonate, sodium carbonate, potassium carbonate, etc.) may be added thereto. The reaction temperature is 0° C. to 50° C., preferably 20° C. to 35° C. The reaction time is 3 hr to 7 hr, preferably 5 hr. The molar ratio of compound [V] and compound [IV] or a salt thereof is 1:1 to 1:1.2, preferably 1:1.1. The amount of the condensing agent is 1.1 equivalent to 1.3 equivalent, preferably 1.2 equivalent, relative to compound [V]. The amount of the reaction accelerator is 0.1 equivalent to 1.0 equivalent, preferably 0.2 equivalent, relative to compound [V]. When a base is used, the amount thereof is preferably 1 equivalent relative to the salt of compound [IV].

Step 8

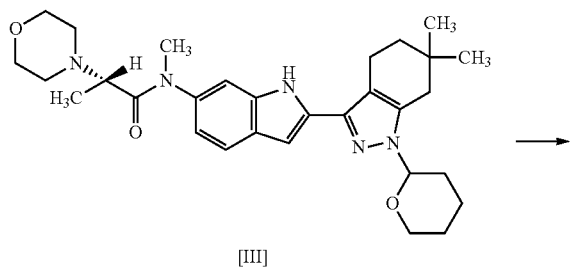

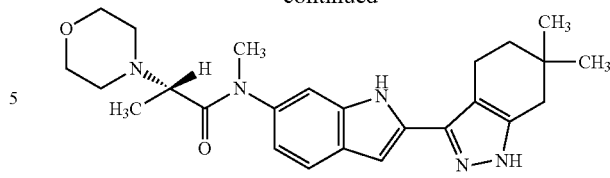

N-[2-(6,6-Dimethyl-4,5,6,7-tetrahydro-1H-indazol-3-yl)-1H-indol-6-yl]-N-methyl-(2S)-2-(morpholin-4-yl)propanamide (compound [I]) can be obtained by reacting compound [III] in the presence of an inorganic acid (hydrogen chloride, hydrogen bromide, etc.), in an ether solvent (cyclopentyl methyl ether, tetrahydrofuran, dimethyl ether, diethyl ether, etc.) or in a mixed solvent of an ester solvent (ethyl acetate, etc.) and an alcohol (methanol, ethanol, 1-propanol, 2-propanol, etc.), or in an alcohol (methanol, ethanol, 1-propanol, 2-propanol, etc.) alone. The reaction temperature is 40° C. to 70° C., preferably 50° C. to 60° C. The reaction time is 30 min to 4 hr, preferably 3.5 hr. The amount of the inorganic acid is 2 to 4 equivalent, preferably 3 equivalent, relative to compound [III]. The solvent for extraction on neutralization with aqueous sodium hydroxide solution and on washing is preferably cyclopentyl methyl ether.

Step 9

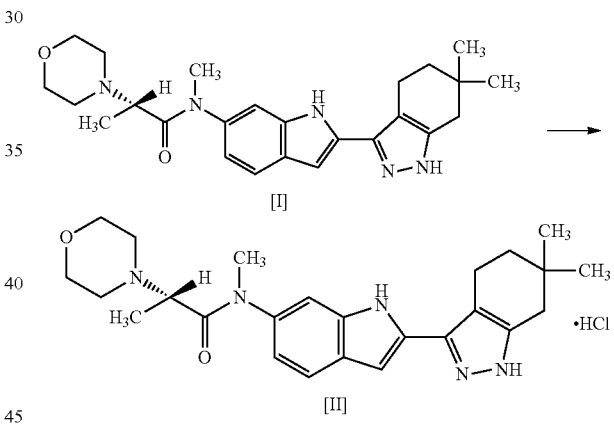

N-[2-(6,6-Dimethyl-4,5,6,7-tetrahydro-1H-indazol-3-yl)-1H-indol-6-yl]-N-methyl-(2S)-2-(morpholin-4-yl)propanamide monohydrochloride (compound [II]) can be obtained by reacting compound [I] with hydrogen chloride in an alcohol (methanol, ethanol, 1-propanol, 2-propanol, etc.), an ester solvent (ethyl acetate, etc.) or a mixed solvent thereof. The amount of the hydrogen chloride is 0.9 equivalent to 1.2 equivalent, preferably 1.05 equivalent, relative to compound [I]. The reaction temperature is 40° C. to 70° C., preferably 50° C. to 60° C. The reaction time is 30 min to 2 hr, preferably 1.5 hr. Compound [II] can be precipitated as a crystal by lowering the reaction temperature to 0° C. to 30° C.

The purification of compound [II] is performed using an alcohol (ethanol, 1-propanol, 2-propanol, etc.) alone, a mixed solvent of an alcohol (ethanol, 1-propanol, 2-propanol, etc.) and an ether solvent (cyclopentyl methyl ether, tetrahydrofuran, etc.), or a mixed solvent of an alcohol (ethanol, 1-propanol, 2-propanol, etc.) and an ester solvent (ethyl acetate, etc.), preferably 1-propanol.

The purified compound [II] can be obtained by suspending the obtained crystals of compound [II] in a solvent, and then by continuously stirring at the temperature of 90° C. to 100° C. for 6 hr or more, subsequently at 0° C. to 30° C. for 1 hr or more.

Specific features of the production method of the present invention are as follows.

(A) Compound [V] can be obtained from compound [VI] by the progress of the following five reactions due one reduction reaction:
(1) removal of benzyloxycarbonyl bonding to amino at the 4-position on the phenyl,
(2) reduction of nitro at the 2-position on the phenyl,
(3) removal of benzyl from the benzyl 3-oxopropanoate moiety,
(4) formation of the indole ring by condensation and cyclization reaction of the amino formed by the reduction in (2) and the oxo group of the 3-oxopropanoic acid moiety formed in (3), and
(5) decarboxylation reaction after the formation of the indole ring.

(B) It is important that the 1-position on the 4,5,6,7-tetrahydro-1H-indazole moiety is protected for the following reasons (1) and (2).
(1) When compound [VIII] is used instead of compound [VII] in the reaction of the above-mentioned Step 5, compound [XI] is introduced into not only the 2-position on the benzyl 3-oxopropanoate moiety, but also the 1-position on the 4,5,6,7-tetrahydro-1H-indazole moiety.
(2) In the reaction of the above-mentioned Step 7, compound [IV] is introduced into not only the methylamino at the 6-position on the indole, but also the 1-position on the 4,5,6,7-tetrahydro-1H-indazole moiety. In fact, in Step 2 of Example 4 in WO 2011/065402, N-{2-(6,6-dimethyl-4,5,6,7-tetrahydro-1H-indazol-3-yl)-1H-indol-6-yl}-N-methylamine is reacted with an amount of 4.6 equivalent of (S)-2-(morpholin-4-yl)propionic acid, together with addition of a base.

As is clear from the below-mentioned Examples, by protecting the 1-position on the 4,5,6,7-tetrahydro-1H-indazole moiety, the amount of compound [IV] can be reduced to 1 to 1.2 equivalent, preferably 1.1 equivalent, relative to compound [V].

(C) The tetrahydropyranyl protecting the 1-position on the 4,5,6,7-tetrahydro-1H-indazole moiety serves as a protecting group without being removed in the following steps (1) to (3):
(1) the reaction under a basic condition for the production of 30 compound [VI] by reacting compound [VII] with compound [XI],
(2) the reduction reaction for the production of compound [V] from compound [VI], and
(3) the amide bond-forming reaction for the production of compound [III] by reacting compound [V] with compound [IV].

(D) The protecting groups exemplified in the following (1) or (2), which may be considered as a protecting group of the 1-position on the 4,5,6,7-tetrahydro-1H-indazole moiety, cannot be used for the reasons described therein.
(1) When tert-butoxycarbonyl is used, the tert-butoxycarbonyl is removed under a basic condition in the above-mentioned Step 5.
(2) When trimethylsilylethoxymethyl is used, the by-product derived from trimethylsilylethoxymethyl after deprotection in the above-mentioned Step 8 can hardly be removed.

(E) The tetrahydropyranyl in compound [III] is removed under a mild acidic condition during the conversion into compound [I], and the by-product derived from tetrahydropyranyl can be easily removed.
(F) Compound [V] having tetrahydropyranyl at the 1-position on the 4,5,6,7-tetrahydro-1H-indazole moiety can be obtained as a crystal. Compound [V] can be obtained with a high purity by crystallization, since the color substance produced in the reaction can be removed, and the like. Therefore, compound [III], compound [I] and compound [II] can be obtained with a high purity in a high-yield in the next step or later.
(G) The intermediates industrially produced during the manufacture of medicinal chemicals are required to be safe for operation. While compound [XI] and compound [VI] have nitro respectively, the low possibility of runaway reaction, the low self-decomposition risk, and the like were deduced from the results of drop-hammer sensitivity measurement, friction sensitivity measurement, differential scanning calorimetry (DSC) measurement and accelerating rate calorimeter (ARC) measurement.

As described in the above-mentioned (A) to (G), compound [XI], compound [VIII], compound [VII], compound [VI], compound [V] and compound [III] used for the production method of the present invention are useful compounds in order to obtain compound [I].

EXAMPLES

The present invention is explained in more detail in the following by referring to Examples, which are not to be construed as limitative.

Example 1

Synthesis of benzyl (4-fluoro-3-nitrophenyl)carbamate

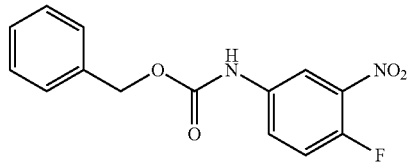

[XII-1]

Under nitrogen atmosphere, sodium hydrogencarbonate (13.9 g, 166 mmol) was dissolved in water (200 mL), and ethyl acetate (150 mL) and 4-fluoro-3-nitroaniline (20.0 g, 128 mmol) were added thereto. Benzyl chloroformate (24.1 g, 141 mmol) was added dropwise thereto at the internal temperature of 30° C. or lower. The used container was washed with ethyl acetate (10 mL), and the washings were also added dropwise thereto. After the completion of the addition, the mixture was stirred at room temperature for 3 hr, left to stand for a while, and separated. The obtained organic layer was filtered, and the filtrate was washed twice with 5 w/w % brine (100 mL), and concentrated under reduced pressure until the volume became about 80 mL. To this concentrated residue was added heptane (60 mL) at the internal temperature of 30° C. to 40° C., and the mixture was stirred at the same temperature for 30 min. Additional heptane (260 mL) was added thereto, and the mixture was stirred at room temperature for 2 hr. The precipitated crystals were collected by filtration, and the obtained wet crystals were washed with a mixed solution of ethyl acetate (6 mL) and heptane (54 mL). The wet crystals were dried under reduced pressure at the external temperature of 50° C. to give benzyl 4-fluoro-3-nitrophenylcarbamate (34.6 g, yield 93.0%).

$^1$H-NMR (400 Mz, DMSO-d$_6$, δ):10.26(brs, 1H(NH)), 8.32(dd, J=6.7, 2.5 Hz, 1H), 7.74(ddd, J=9.1, 3.9, 2.8 Hz, 1H), 7.52(dd, J=11.1, 9.0 Hz, 1H), 7.45-7.31(m, 5H), 5.17(s, 2H)

Example 2

Synthesis of benzyl N-(4-fluoro-3-nitrophenyl)-N-methylcarbamate

[XI-1]

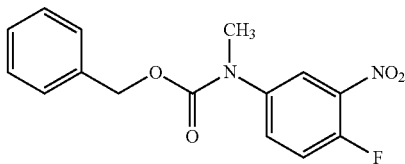

Under nitrogen atmosphere, benzyl 4-fluoro-3-nitrophenylcarbamate (20.0 g, 68.9 mmol) was dissolved in N,N-dimethylformamide (120 mL), and cesium carbonate (26.9 g, 82.7 mmol) was added thereto. Methyl iodide (11.7 g, 82.7 mmol) was added dropwise thereto at the internal temperature of 25° C. or lower, and the mixture was stirred at the internal temperature of 20° C. to 30° C. for 3 hr. After the completion of the reaction, toluene (200 mL) was added thereto, and water (100 mL) was added thereto at the internal temperature of 35° C. or lower. This solution was stirred for about 10 min, left to stand for a while, and separated. The obtained organic layer was washed twice with water (100 mL), and concentrated under reduced pressure until the volume became about 100 mL. To this concentrated residue was added heptane (100 mL) at the internal temperature of 30° C. to 40° C., and the mixture was stirred at the same temperature for 30 min. Additional heptane (140 mL) was added thereto, and the mixture was stirred at room temperature for 1 hr. The precipitated crystals were collected by filtration, and the obtained wet crystals were washed with a mixed solution of toluene (6 mL) and heptane (54 mL). The wet crystals were dried under reduced pressure at the external temperature of 50° C. to give benzyl N-(4-fluoro-3-nitrophenyl)-N-methylcarbamate (19.3 g, yield 91.9%).

$^1$H-NMR (400 Mz, DMSO-d$_6$, δ):8.17(dd, J=6.7, 2.8 Hz, 1H), 7.81(ddd, J=9.0, 3.9, 2.8 Hz, 1H), 7.59(dd, J=11.3, 9.0 Hz, 1H), 7.38-7.27(m, 5H), 5.13(s, 2H), 3.28(s, 3H)

friction sensitivity: JIS grade 7 drop-hammer sensitivity: JIS grade 8

Differential scanning calorimetry (DSC) measurement of benzyl N-(4-fluoro-3-nitrophenyl)-N-methylcarbamate Decomposition exothermic onset temperature: 272.5° C.

decomposition calorimetry: 1.33 kJ/g measurement conditions sample: 1.470 mg container: SUS pressure tight sealed cell rate of temperature increase: 10° C./min Example 3

Synthesis of benzyl 3-(6,6-dimethyl-4,5,6,7-tetrahydro-1H-indazol-3-yl)-3-oxopropanoate

[VIII-1]

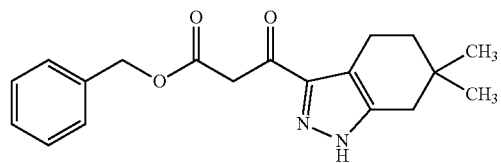

Step 1: Under nitrogen atmosphere, 6,6-dimethyl-4,5,6,7-tetrahydro-1H-indazole-3-carboxylic acid (10.0 g, 51.5 mmol) and 1,1'-carbonyldiimidazole (9.19 g, 56.7 mmol) were suspended in tetrahydrofuran (60 mL), to the suspension was added dropwise N,N-dimethylformamide (20 mL), and the mixture was stirred at the internal temperature of 20° C. to 30° C. for 1 hr (solution (1)).

Step 2: Under nitrogen atmosphere, magnesium chloride (19.6 g, 206 mmol) and monobenzyl potassium malonate (23.9 g, 103 mmol) were suspended in tetrahydrofuran (80 mL) in another reaction container, and to the suspension was added dropwise N,N-dimethylformamide (80 mL) at the internal temperature of 20° C. to 50° C. The mixture was stirred at the internal temperature of 60° C. for 30 min, the solution (1) was added thereto, and the mixture was stirred at the internal temperature of 60 to 65° C. for 3 hr. After the completion of the reaction, toluene (100 mL) was added thereto, and 10% citric acid solution (100 mL) was added thereto at the internal temperature of 35° C. or lower. This solution was stirred for about 10 min, and separated, and the obtained organic layer was washed successively with 10% citric acid solution (100 mL), 5% aqueous sodium bicarbonate (100 mL) and water (50 mL×2). The organic layer was concentrated under reduced pressure until the volume became about 20 mL, heptane (40 mL) was added thereto, and the mixture was stirred at the internal temperature of 50° C. to 60° C. for 30 min. Heptane (40 mL) was added dropwise thereto at the internal temperature of 45° C. to 55° C., and the mixture was stirred at the same temperature for 30 min, and then at room temperature for 2 hr. The precipitated crystals were collected by filtration, and the obtained wet crystals were washed with a mixed solution of toluene (5 mL) and heptane (45 mL). The wet crystals were dried under reduced pressure at the external temperature of 40° C. to give benzyl 3-(6,6-dimethyl-4,5,6,7-tetrahydro-1H-indazol-3-yl)-3-oxopropanoate (14.1 g, yield 83.6%).

$^1$H-NMR (400 Mz, DMSO-d$_6$, δ):13.07(brs, 1H(NH)), 7.37-7.27(m, 5H), 5.11(s, 2H), 4.02(s, 2H), 2.60(t, J=6.1 Hz, 2H), 2.37(s, 2H), 1.44(t, J=6.4 Hz, 2H), 0.93(s, 6H)

Example 4-1

Synthesis of benzyl 3-[6,6-dimethyl-1-(tetrahydropyran-2-yl)-4,5,6,7-tetrahydro-1H-indazol-3-yl]-3-oxopropanoate

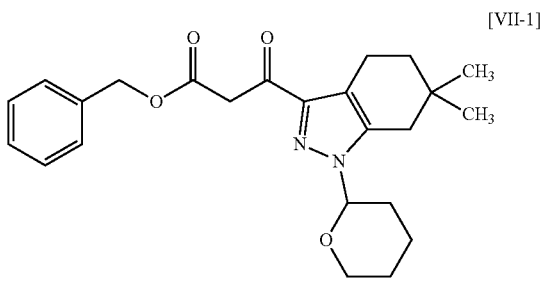 [SMILES: CC1(C)CCc2c(C(=O)CC(=O)OCc3ccccc3)nn(C3CCCCO3)c2C1]

[VII-1]

Under nitrogen atmosphere, benzyl 3-(6,6-dimethyl-4,5,6,7-tetrahydro-1H-indazol-3-yl)-3-oxopropanoate (10.0 g, 30.6 mmol) was dissolved in ethyl acetate (80 mL), to this solution were successively added p-toluenesulfonic acid (0.29 g, 1.53 mmol) and 3,4-dihydro-2H-pyran (3.86 g, 45.9 mmol), and the mixture was stirred at the internal temperature of 15° C. to 25° C. for 4 hr. After the completion of the reaction, 5 w/w % aqueous sodium hydrogencarbonate solution (40 mL) was added thereto, and the mixture was stirred for 10 min, left to stand for a while, and separated. The obtained organic layer was washed with 10 w/w % brine (40 mL), dried over magnesium sulfate, and filtered. The organic layer was concentrated under reduced pressure, and the concentrated residue was dissolved in a mixed solution of hexane and ethyl acetate (4:1), and purified by silica gel chromatography to give benzyl 3-[6,6-dimethyl-1-(tetrahydropyran-2-yl)-4,5,6,7-tetrahydro-1H-indazol-3-yl]-3-oxopropanoate (12 g, yield 95.2%).

The obtained compound in this step is deduced to be a mixture of R-form and S-form, but its ratio is not measured.

$^1$H-NMR (400 Mz, DMSO-d$_6$, δ): 7.37-7.27(m, 5H), 5.40(dd, J=9.4, 2.7 Hz, 1H), 5.11(s, 2H), 4.01(dd, J=25.7, 15.7 Hz, 2H), 3.83(d, J=11.1 Hz, 1H), 3.61(ddd, J=12.4, 8.0, 3.3 Hz, 1H), 2.60(dt, J=22.3, 8.7 Hz, 2H), 2.45(dd, J=47.3, 17.0 Hz, 2H), 2.16(tt, J=15.0, 5.3 Hz, 1H), 2.00-1.90(m, 1H), 1.85-1.77(m, 1H), 1.70-1.55(m, 1H), 1.55-1.45(m, 2H), 1.44(t, J=6.4 Hz, 2H), 0.94(d, J=12.3 Hz, 6H)

Example 4-2

Synthesis of benzyl 3-[6,6-dimethyl-1-(tetrahydropyran-2-yl)-4,5,6,7-tetrahydro-1H-indazol-3-yl]-3-oxopropanoate

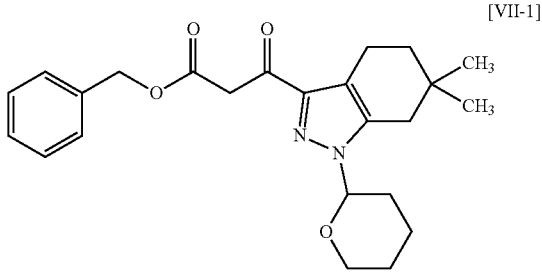 [SMILES: CC1(C)CCc2c(C(=O)CC(=O)OCc3ccccc3)nn(C3CCCCO3)c2C1]

[VII-1]

Under nitrogen atmosphere, benzyl 3-(6,6-dimethyl-4,5,6,7-tetrahydro-1H-indazol-3-yl)-3-oxopropanoate (20.0 g, 61.3 mmol) was dissolved in ethyl acetate (150 mL), and to this solution were successively added p-toluenesulfonic acid (1.17 g, 6.13 mmol) and dihydropyran (7.73 g, 92.0 mmol). The used container was washed with ethyl acetate (10 mL), and the washings were also added thereto. The mixture was stirred at the internal temperature of 15° C. to 30° C. for 2.5 hr, 5 w/w % aqueous sodium hydrogencarbonate solution (40 mL) was added thereto, and the mixture was stirred for a while, and separated. The obtained organic layer was washed with 10 w/w % brine (80 mL), and concentrated under reduced pressure until the volume became about 60 mL. To the concentrated residue was added ethyl acetate (100 mL), and the mixture was again concentrated under reduced pressure until the volume became about 60 mL. To the concentrated residue was added ethyl acetate (100 mL), and the mixture was again concentrated under reduced pressure until the volume became about 60 mL. To the concentrated residue was added N,N-dimethylacetamide (60 mL), and the mixture was again concentrated under reduced pressure until the volume became about 80 mL to give a solution of benzyl 3-[6,6-dimethyl-1-(tetrahydropyran-2-yl)-4,5,6,7-tetrahydro-1H-indazol-3-yl]-3-oxopropanoate.

The obtained compound in this step is deduced to be a mixture of R-form and S-form, but its ratio is not measured.

Example 5-1

Synthesis of benzyl 2-[4-(N-benzyloxycarbonyl-N-methylamino)-2-nitrophenyl]-3-[6,6-dimethyl-1-(tetrahydropyran-2-yl)-4,5,6,7-tetrahydro-1H-indazol-3-yl]-3-oxopropanoate

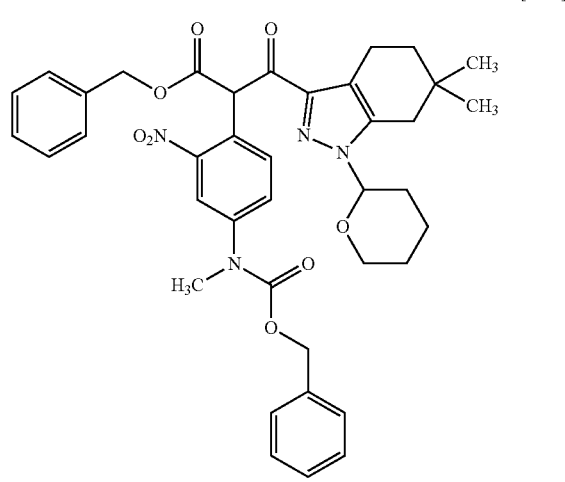 [SMILES: CN(C(=O)OCc1ccccc1)c1ccc(C(C(=O)OCc2ccccc2)C(=O)c2nn(C3CCCCO3)c3c2CCC(C)(C)C3)c([N+](=O)[O-])c1]

[VI-1]

Under nitrogen atmosphere, to a solution of benzyl 3-[6,6-dimethyl-1-(tetrahydropyran-2-yl)-4,5,6,7-tetrahydro-1H-indazol-3-yl]-3-oxopropanoate (142 mg, 0.346 mmol) in dimethyl sulfoxide (0.71 mL) were successively added benzyl N-(4-fluoro-3-nitrophenyl)-N-methylcarbamate (100 mg, 0.329 mmol) and potassium carbonate (96 mg, 0.692 mmol), and the mixture was stirred in an oil bath of 90° C. for 2 hr and 20 min. After the completion of the reaction, the reaction solution was cooled to room temperature, and poured into 5 w/w % aqueous citric acid solution. Then, the mixture was extracted with ethyl acetate, and separated, and the obtained organic layer was washed successively with water and saturated brine. The obtained organic layer was dried over anhydrous sodium sulfate, the anhydrous sodium sulfate was removed by filtration, and the filtrate was concentrated under reduced pressure. The residue was purified by column chromatography (hexane:ethyl acetate 3:1 to 2:1) to give benzyl 2-[4-(N-benzyloxycarbonyl-N-methylamino)-2-nitrophenyl]-3-[6,6-dimethyl-1-(tetrahydropyran-2-yl)-4,5,6,7-tetrahydro-1H-indazol-3-yl]-3-oxopropanoate (184 mg, yield 81%).

The obtained compound in this step is deduced to be a mixture of diastereomers and/or tautomers, but its ratio is not measured.

$^1$H-NMR (DMSO-D$_6$, δ): 8.11(dd, J=13.9, 2.4 Hz, 1H), 7.74(td, J=8.2, 2.4 Hz, 1H), 7.45(dd, J=8.5, 3.0 Hz, 1H), 7.39-7.23(m, 10H), 6.32(d, J=9.0 Hz, 1H), 5.43-5.34(m, 1H), 5.26-5.18(m, 2H), 5.16(d, J=4.4 Hz, 2H), 3.81-3.68(m, 1H), 3.64-3.52(m, 1H), 3.31(d, J=5.3 Hz, 3H), 2.65-2.56(m, 2H), 2.55-2.30(m, 2H), 2.12-2.00(m, 1H), 1.97-1.82(m, 1H), 1.77-1.67(m, 1H), 1.67-1.35(m, 5H), 0.94 (dd, J=11.9, 6.0 Hz, 6H)

Differential scanning calorimetry (DSC) measurement of benzyl 2-[4-(N-benzyloxycarbonyl-N-methylamino)-2-nitrophenyl]-3-[6,6-dimethyl-1-(tetrahydropyran-2-yl)-4,5,6,7-tetrahydro-1H-indazol-3-yl]-3-oxopropanoate Decomposition exothermic onset temperature: 120.8° C.
decomposition calorimetry: 848.3 J/g
measurement conditions
  sample: 3.390 mg
  container: SUS pressure tight sealed cell
  rate of temperature increase: 10° C./min Example 5-2

Synthesis of benzyl 2-[4-(N-benzyloxycarbonyl-N-methylamino)-2-nitrophenyl]-3-[6,6-dimethyl-1-(tetrahydropyran-2-yl)-4,5,6,7-tetrahydro-1H-indazol-3-yl]-3-oxopropanoate

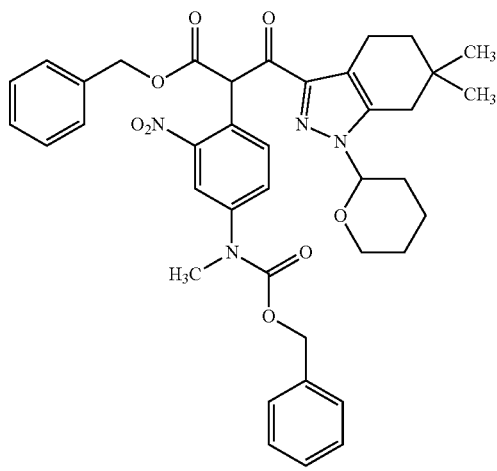

[VI-1]

Under nitrogen atmosphere, to a solution of benzyl 3-[6,6-dimethyl-1-(tetrahydropyran-2-yl)-4,5,6,7-tetrahydro-1H-indazol-3-yl]-3-oxopropanoate, which was obtained in Example 4-2, were successively added benzyl N-(4-fluoro-3-nitrophenyl)-N-methylcarbamate (18.6 g, 61.3 mmol) and tripotassium phosphate (32.5 g, 153 mmol), the used container was washed with N,N-dimethylacetamide (20 mL), and the washings were also added thereto. The mixture was stirred at the internal temperature of 50° C. to 60° C. for 23 hr, and then at the internal temperature of 70° C. to 80° C. for 5.5 hr. After the completion of the reaction, toluene (100 mL) was added thereto at the internal temperature of 40° C. or lower, and water (160 mL) was added thereto at the internal temperature of 30° C. or lower. This solution was stirred at room temperature for about 30 min, and separated, and the obtained organic layer was washed successively with 10 w/w % aqueous citric acid solution (80 mL), 5 w/w % aqueous sodium hydrogencarbonate solution (80 mL) and 10 w/w % brine (80 mL). The obtained organic layer was concentrated under reduced pressure until the volume became about 80 mL to give a solution of benzyl 2-[4-(N-benzyloxycarbonyl-N-methylamino)-2-nitrophenyl]-3-[6,6-dimethyl-1-(tetrahydropyran-2-yl)-4,5,6,7-tetrahydro-1H-indazol-3-yl]-3-oxopropanoate.

The obtained compound in this step is deduced to be a mixture of diastereomers and/or tautomers, but its ratio is not measured.

Example 6

Synthesis of N-[2-[6,6-dimethyl-1-(tetrahydropyran-2-yl)-4,5,6,7-tetrahydro-1H-indazol-3-yl]-1H-indol-6-yl]-N-methylamine

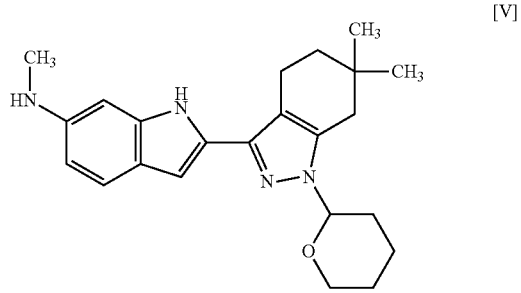 [SMILES: CNc1ccc2cc(-c3nn(C4CCCCO4)c4c3CCC(C)(C)C4)[nH]c2c1]

[V]

A solution of benzyl 2-[4-(N-benzyloxycarbonyl-N-methylamino)-2-nitrophenyl]-3-[6,6-dimethyl-1-(tetrahydropyran-2-yl)-4,5,6,7-tetrahydro-1H-indazol-3-yl]-3-oxopropanoate, which was obtained in Example 5-2, was charged into a pressure tight bottle, the used container was washed with toluene (20 mL), and the washings were also added thereto. Then, methanol (120 mL) and 5 w/w % palladium on carbon (PE type, 50% wet, 4.0 g) were added thereto, the reaction system was purged with hydrogen, and the mixture was stirred under hydrogen pressure of 3 atm to 4 atm for 24 hr. After the completion of the reaction, tetrahydrofuran (140 mL) was added thereto, and the precipitated crystals were dissolved. The palladium on carbon was removed by filtration, and washed with tetrahydrofuran (20 mL). The obtained filtrate and the washings were combined, and concentrated under reduced pressure until the volume became about 60 mL. To the concentrated residue was added toluene (100 mL), and the mixture was again concentrated under reduced pressure until the volume became about 60 mL. To the concentrated residue was added toluene (100 mL), and the mixture was again concentrated under reduced pressure until the volume became about 60 mL. To the obtained concentrated residue was added 2-propanol (40 mL) at the internal temperature of 45° C. to 55° C., and the mixture was stirred at the same temperature for 1 hr, and then at room temperature for 1 hr. The precipitated crystals were collected by filtration, and the obtained wet crystals were washed with a mixed solution of toluene (8 mL) and 2-propanol (32 mL). The wet crystals were dried under reduced pressure at the external temperature of 50° C. to give N-[2-[6,6-dimethyl-1-(tetrahydropyran-2-yl)-4,5,6,7-tetrahydro-1H-indazol-3-yl]-1H-indol-6-yl]-N-methylamine (18.5 g, yield 79.8%, LC purity 99.3%).

The obtained compound in this step is deduced to be a mixture of R-form and S-form, but its ratio is not measured.

$^1$H-NMR (400 Mz, DMSO-$d_6$, δ):10.60 (d, J=1.4 Hz, 1H), 7.19 (d, J=8.5 Hz, 1H), 6.50(d, J=1.9 Hz, 1H), 6.40-6.35(m, 2H), 5.36-5.29(m, 2H), 3.92(d, J=11.8 Hz, 1H), 3.58-3.66 (m, 1H), 2.68(d, J=5.1 Hz, 3H), 2.60(t, J=6.0 Hz, 2H), 2.34-2.45(m, 2H), 2.08-1.99(m, 1H), 1.86(dd, J=13.0, 2.7 Hz, 1H), 1.75-1.62(m, 1H), 1.55(t, J=6.2 Hz, 4H), 1.01(d, J=10.9 Hz, 6H)

LC analysis condition for N-[2-[6,6-dimethyl-1-(tetrahydropyran-2-yl)-4,5,6,7-tetrahydro-1H-indazol-3-yl]-1H-indol-6-yl]-N-methylamine column: YMC-triart C18 5 μm 4.6×150 mm column temperature: constant temperature around 40° C.

mobile phase A: 10 mmol/L phosphate buffer solution mobile phase B: MeCN gradient condition:

TABLE 1

| | Time (min) | | | | | |
|---|---|---|---|---|---|---|
| | 0 | 2 | 10 | 19 | 20 | 25 |
| mobile phase A (%) | 90 | 90 | 10 | 10 | 90 | 90 |
| mobile phase B (%) | 10 | 10 | 90 | 90 | 10 | 10 | flow rate: 1.5 mL/min detection method: UV 254 nm injected amount: 10 μL analysis time: 20 min retention time: about 10.0 min preparation method of mobile phase A: $NaH_2PO_4 \cdot 2H_2O$ (2.34 g) is dissolved in water (3 L), and 85% $H_3PO_4$ (1.0 mL) is added thereto. This solution is filtered through a filter (0.45 μm), and the filtrate is degassed well, and then used for LC analysis.

powder X-ray diffraction measurement of N-[2-[6,6-dimethyl-1-(tetrahydropyran-2-yl)-4,5,6,7-tetrahydro-1H-indazol-3-yl]-1H-indol-6-yl]-N-methylamine The sample was fixed on an aluminium cell, and powder X-ray diffraction was measured using powder X-ray diffraction apparatus (PANalytical X' pert Pro) under the condition of X-ray source: Cu, tube voltage: 45 kV, tube current: 40 mA, scan speed: 0.418°/sec, step width: 0.0334° and diffraction angle: 3° to 25° to give a diffraction pattern. The obtained diffraction pattern is shown in FIG. 1.

diffraction peak: 2θ=9.59, 10.6, 11.0, 11.7, 14.0, 14.4, 14.8, 15.1, 16.7, 17.9, 18.7, 18.9, 19.2, 19.8, 20.1, 20.4, 20.6, 20.9, 21.6, 21.9, 23.3, 23.9, 24.2, 24.5°.

Example 7-1

N-[2-(6,6-dimethyl-1-(tetrahydropyran-2-yl)-4,5,6,7-tetrahydro-1H-indazol-3-yl)-1H-indol-6-yl]-N-methyl-(2S)-2-(morpholin-4-yl)propanamide

[III]

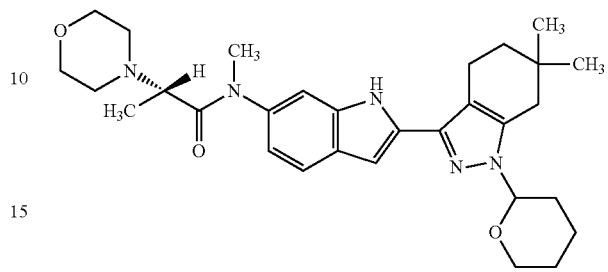

Under nitrogen atmosphere, N-[2-[6,6-dimethyl-1-(tetrahydropyran-2-yl)-4,5,6,7-tetrahydro-1H-indazol-3-yl]-1H-indol-6-yl]-N-methylamine (1.50 g, 3.96 mmol) was dissolved in N,N-dimethylformamide (7.5 mL), and (S)-2-(morpholin-4-yl)propanoic acid (694 mg, 4.36 mmol), 1-hydroxybenzotriazole monohydrate (606 mg, 3.96 mmol) and 1-ethyl-3-(3-dimethylaminopropyl)carbodiimide hydrochloride (836 mg, 4.36 mmol) were successively added thereto at room temperature, and the mixture was stirred at room temperature for 5 hr. After the completion of the reaction, the reaction solution was poured into aqueous sodium hydrogencarbonate solution, and the mixture was stirred at the same temperature for 30 min. The precipitated solid was collected by filtration, and washed successively with aqueous sodium hydrogencarbonate solution and water. The obtained wet crystals were dried to give N-[2-(6,6-dimethyl-1-(tetrahydropyran-2-yl)-4,5,6,7-tetrahydro-1H-indazol-3-yl)-1H-indol-6-yl]-N-methyl-(2S)-2-(morpholin-4-yl)propanamide (1.92 g, yield 93%).

The obtained compound in this step is deduced to be a mixture of SR-form and SS-form, but its ratio is not measured.

$^1$H-NMR (DMSO-$D_6$, δ): 11.31(s, 1H), 7.54 (d, J=8.1 Hz, 1H), 7.31(s, 1H), 6.89(d, J=8.1 Hz, 1H), 6.63(s, 1H), 5.34(d, J=9.7 Hz, 1H), 3.97-3.87(m, 1H), 3.69-3.56(m, 1H), 3.52-3.43(m, 4H), 3.20-3.15(m, 4H), 2.69-2.60(m, 2H), 2.57-2.33 (m, 5H), 2.30-2.18(m, 2H), 2.07-1.96(m, 1H), 1.92-1.82(m, 1H), 1.75-1.61(m, 1H), 1.61-1.46(m, 4H), 1.05-0.94(m, 3H), 1.01(d, J=9.0 Hz, 6H)

Example 7-2

N-[2-(6,6-dimethyl-1-(tetrahydropyran-2-yl)-4,5,6,7-tetrahydro-1H-indazol-3-yl)-1H-indol-6-yl]-N-methyl-(2S)-2-(morpholin-4-yl)propanamide

[III]

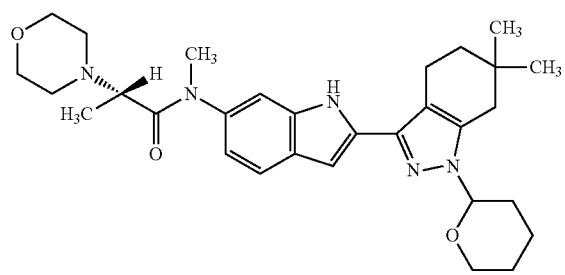

Under nitrogen atmosphere, N-[2-[6,6-dimethyl-1-(tetrahydropyran-2-yl)-4,5,6,7-tetrahydro-1H-indazol-3-yl]-1H-indol-6-yl]-N-methylamine (10.0 g, 26.4 mmol) was dissolved in N,N-dimethylformamide (50 mL), and (S)-2-(morpholin-4-yl)propanoic acid monohydrochloride (5.67 g, 29.0 mmol), sodium hydrogencarbonate (2.44 g, 29.0 mmol), 1-hydroxybenzotriazole monohydrate (0.81 g, 5.28 mmol) and 1-ethyl-3-(3-dimethylaminopropyl)carbodiimide hydrochloride (6.08 g, 31.7 mmol) were successively added thereto at room temperature, and the mixture was stirred at the internal temperature of 20° C. to 35° C. for 5 hr. After the completion of the reaction, cyclopentyl methyl ether (100 mL) and 10 w/w % brine (50 mL) were added thereto at the internal temperature of 0° C. to 30° C., and the mixture was stirred at the same temperature for 30 min. The mixture was left to stand for a while, and separated, and the obtained organic layer was concentrated under reduced pressure until the volume became about 30 mL. To the concentrated residue was added cyclopentyl 5 methyl ether (70 mL), and the mixture was again concentrated under reduced pressure until the volume became about 30 mL. To the concentrated residue was added cyclopentyl methyl ether (70 mL), and the mixture was again concentrated under reduced pressure until the volume became about 30 mL. The volume was adjusted to about 60 mL by addition of cyclopentyl methyl ether to give a solution of N-[2-(6,6-dimethyl-1-(tetrahydropyran-2-yl)-4,5,6,7-tetrahydro-1H-indazol-3-yl)-1H-indol-6-yl]-N-methyl-(2S)-2-(morpholin-4-yl)propanamide.

The obtained compound in this step is deduced to be a mixture of SR-form and SS-form, but its ratio is not measured.

Example 8-1

Synthesis of N-[2-(6,6-dimethyl-4,5,6,7-tetrahydro-1H-indazol-3-yl)-1H-indol-6-yl]-N-methyl-(2S)-2-(morpholin-4-yl)propanamide

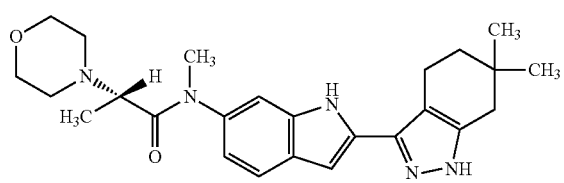

[I]

Under nitrogen atmosphere, N-[2-(6,6-dimethyl-1-(tetrahydropyran-2-yl)-4,5,6,7-tetrahydro-1H-indazol-3-yl)-1H-indol-6-yl]-N-methyl-(2S)-2-(morpholin-4-yl)propanamide (1.88 g, 3.62 mmol) was dissolved in methanol (18.8 mL), and 2N hydrochloric acid (5.43 mL) was added thereto. The mixture was stirred for 2 hr and 10 min in an oil bath of 60° C. After the completion of the reaction, the mixture was cooled to room temperature, and concentrated under reduced pressure. To the residue were added ethyl acetate and water, and the mixture was extracted and separated. To the obtained aqueous layer was added ethyl acetate, and the pH of the mixture was adjusted to 8 with sodium hydrogencarbonate while stirring at room temperature. After extraction and separation, and the obtained organic layer was washed with saturated brine, and dried over anhydrous sodium sulfate. The anhydrous sodium sulfate was removed by filtration, and the filtrate was concentrated under reduced pressure to give N-[2-(6,6-dimethyl-4,5,6,7-tetrahydro-1H-indazol-3-yl)-1H-indol-6-yl]-N-methyl-(2S)-2-(morpholin-4-yl)propanamide (1.52 g, yield 96%).

$^1$H-NMR (DMSO-D$_6$, δ): 12.53(s, 1H), 11.40(s, 1H), 7.53(d, J=8.1 Hz, 1H), 7.27(s, 1H), 6.87(d, J=8.6 Hz, 1H), 6.58(s, 1H), 3.50-3.44(m, 4H), 3.21-3.15(m, 1H), 3.17(s, 3H), 2.65(t, J=6.0 Hz, 2H), 2.47-2.36(m, 4H), 2.30-2.18(m, 2H), 1.56(t, J=6.3 Hz, 2H), 1.00(d, J=16.2 Hz, 3H), 0.99(s, 6H)

Example 8-2

Synthesis of N-[2-(6,6-dimethyl-4,5,6,7-tetrahydro-1H-indazol-3-yl)-1H-indol-6-yl]-N-methyl-(2S)-2-(morpholin-4-yl)propanamide

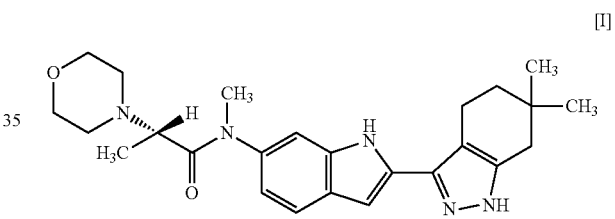

[I]

Under nitrogen atmosphere, to a solution of N-[2-(6,6-dimethyl-1-(tetrahydropyran-2-yl)-4,5,6,7-tetrahydro-1H-indazol-3-yl)-1H-indol-6-yl]-N-methyl-(2S)-2-(morpholin-4-yl)propanamide, which was obtained in Example 7-2, was added dropwise 2N hydrogen chloride-ethanol solution (39.6 mL) at the internal temperature of 15° C. to 60° C., and the mixture was stirred at the internal temperature of 50° C. to 60° C. for 3.5 hr. After the completion of the reaction, this solution was added dropwise to a mixed solution of 1N aqueous sodium hydroxide solution (84.5 mL) and cyclopentyl methyl ether (350 mL) at the internal temperature of 0° C. to 60° C., the used container was washed with ethanol (20 mL), and the washings were also added thereto. After confirming that the pH of the aqueous layer was 9 or more, the mixture was separated at the internal temperature of 40° C. to 50° C., and the obtained organic layer was washed three times with water (100 mL) at the same temperature, and concentrated under reduced pressure until the volume became about 30 mL. To the concentrated residue was added ethyl acetate (70 mL), and the mixture was again concentrated under reduced pressure until the volume became about 30 mL. To the concentrated residue was added ethyl acetate (70 mL), and the mixture was again concentrated under reduced pressure until the volume became about 30 mL to give a solution of N-[2-(6,6-dimethyl-4,5,6,7-tetrahydro-1H-indazol-3-yl)-1H-indol-6-yl]-N-methyl-(2S)-2-(morpholin-4-yl)propanamide.

Example 9

Synthesis of N-[2-(6,6-dimethyl-4,5,6,7-tetrahydro-1H-indazol-3-yl)-1H-indol-6-yl]-N-methyl-(2S)-2-(morpholin-4-yl)propanamide monohydrochloride

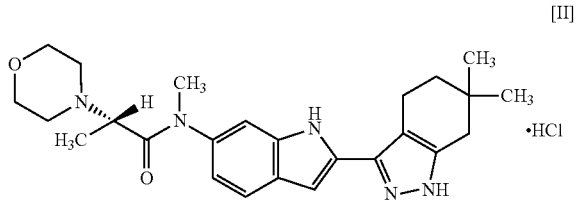 [SMILES: C[C@@H](C(=O)N(C)c1ccc2cc(-c3n[nH]c4c3CCC(C)(C)C4)[nH]c2c1)N1CCOCC1 ; Cl]

[II]

Step 1

To a solution of N-[2-(6,6-dimethyl-4,5,6,7-tetrahydro-1H-indazol-3-yl)-1H-indol-6-yl]-N-methyl-(2S)-2-(morpholin-4-yl)propanamide, which was obtained in Example 8-2, was added 1-propanol (15 mL), and the insoluble substance was removed by filtration. The used container and filter were washed with 1-propanol (15 mL). The filtrate and washings were combined, and 4N hydrogen chloride-ethyl acetate solution (2.64 mL, 10.6 mmol) was added dropwise thereto at the internal temperature of 50° C. to 60° C. The mixture was stirred at the same temperature for 1 hr, and 4N hydrogen chloride-ethyl acetate solution (3.96 mL, 15.8 mmol) was added dropwise thereto. The mixture was stirred at the same temperature for 30 min, ethyl acetate (90 mL) was added dropwise thereto, and the mixture was stirred for 1 hr. The mixture was stirred overnight at room temperature, and the precipitated crystals were collected by filtration. The obtained wet crystals were washed with a mixed solution of 1-propanol (4 mL) and ethyl acetate (16 mL), and then ethyl acetate (20 mL). The wet crystals were dried under reduced pressure at the external temperature of 50° C. to give N-[2-(6,6-dimethyl-4,5,6,7-tetrahydro-1H-indazol-3-yl)-1H-indol-6-yl]-N-methyl-(2S)-2-(morpholin-4-yl)propanamide monohydrochloride (11.0 g, yield 88.0%).

Step 2

Under nitrogen atmosphere, N-[2-(6,6-dimethyl-4,5,6,7-tetrahydro-1H-indazol-3-yl)-1H-indol-6-yl]-N-methyl-(2S)-2-(morpholin-4-yl)propanamide monohydrochloride (4.0 g) was suspended in 1-propanol (18 mL), and the suspension was stirred at the internal temperature of 90° C. to 100° C. for 7.5 hr, and then overnight at room temperature. The crystals were collected by filtration, and the obtained wet crystals were washed with 1-propanol (8 mL). The wet crystals were dried under reduced pressure at the external temperature of 65° C. to give N-[2-(6,6-dimethyl-4,5,6,7-tetrahydro-1H-indazol-3-yl)-1H-indol-6-yl]-N-methyl-(2S)-2-(morpholin-4-yl)propanamide monohydrochloride (3.48 g, yield 87.0%, LC purity 99.9% or more).

$^1$H-NMR (400 Mz, DMSO-d$_6$, δ):11.54(s, 1H), 10.35(brs, 1H), 7.62(d, J=8.3 Hz, 1H), 7.38(s, 1H), 6.98(dd, J=8.3, 1.8 Hz, 1H), 6.65(s, 1H), 4.95-3.75(m, 4H), 3.70(t, J=12.1 Hz, 1H), 3.47-2.96(m, 7H), 2.66(t, J=6.1 Hz, 2H), 2.42(s, 2H), 1.56(t, J=6.4 Hz, 2H), 1.35(d, J=6.5 Hz, 3H), 1.01(s, 6H)

LC analysis condition for N-[2-(6,6-dimethyl-4,5,6,7-tetrahydro-1H-indazol-3-yl)-1H-indol-6-yl]-N-methyl-(2S)-2-(morpholin-4-yl)propanamide monohydrochloride column: YMC-triart C18 5 μm 4.6×150 mm
column temperature: constant temperature around 40° C.
mobile phase A: 20 mmol/L phosphate buffer solution
mobile phase B: MeCN
gradient condition:

TABLE 2

| | Time (min) | | | | |
|---|---|---|---|---|---|
| | 0 | 2 | 10 | 25 | 30 |
| mobile phase A (%) | 80 | 80 | 40 | 40 | 80 |
| mobile phase B (%) | 20 | 20 | 60 | 60 | 20 | flow rate: 1.5 mL/min
detection method: UV 220 nm
injected amount: 10 μL
analysis time: 30 min
retention time: about 12.7 min
preparation method of mobile phase A: KH$_2$PO$_4$ (4.08 g) and K$_2$HPO$_4$ (5.23 g) are exactly weighed, and dissolved in water (3 L). This solution are filtered through a filter (0.45 μm), and the filtrate is degassed well, and then used for LC analysis.

INDUSTRIAL APPLICABILITY

The compound of the present invention is useful as a synthetic intermediate for producing a compound of the formula [II].

The present invention can provide a method for producing a compound of the formula [II] in good yield.

The production method of the present invention can be performed in a few steps without a reagent that needs careful handling due to danger and toxicity, and therefore it is useful as an industrial large-scale synthetic method.

The invention claimed is:
1. A method of producing a compound of the formula [I]

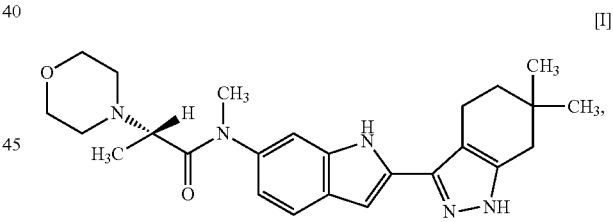

[I]

which comprises a step of removing the protecting group from a compound of the formula [III]

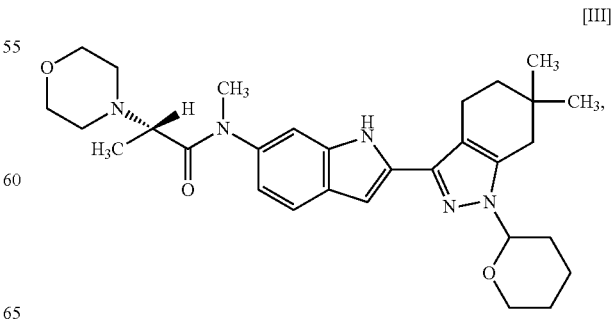

[III]

to give a compound of the formula [I].

2. A method of producing a compound of the formula [II]

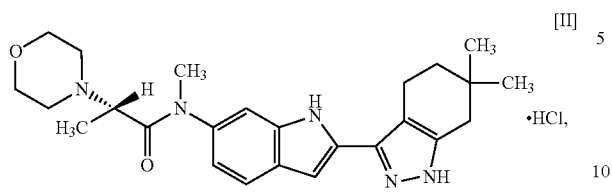

which comprises a step of removing the protecting group from a compound of the formula [III]

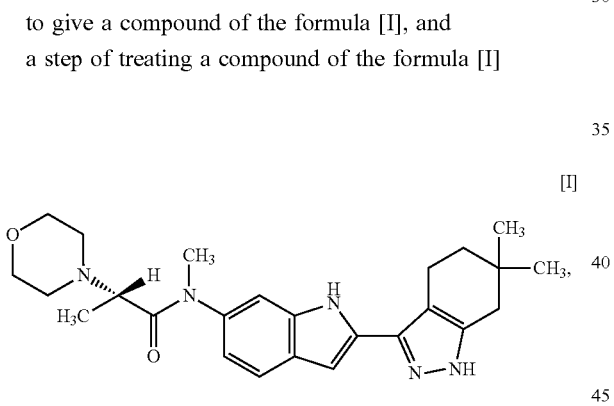

to give a compound of the formula [I], and
a step of treating a compound of the formula [I]

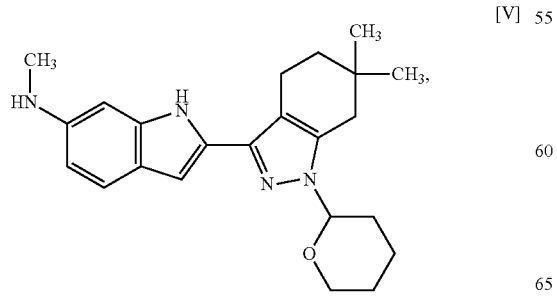

with hydrogen chloride to give a compound of the formula [II].

3. The method of claim 1 or 2, which further comprises a step of reacting a compound of the formula [V]

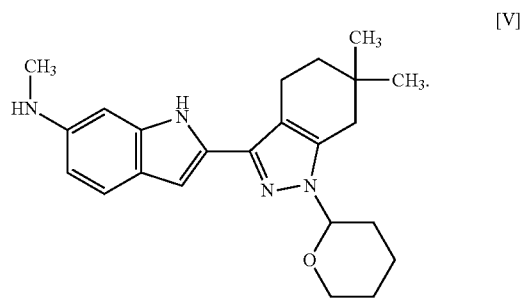

with a compound of the formula [IV]

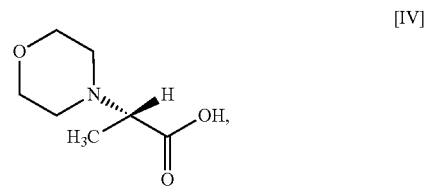

or a reactive derivative thereof or a salt thereof to give a compound of the formula [III]

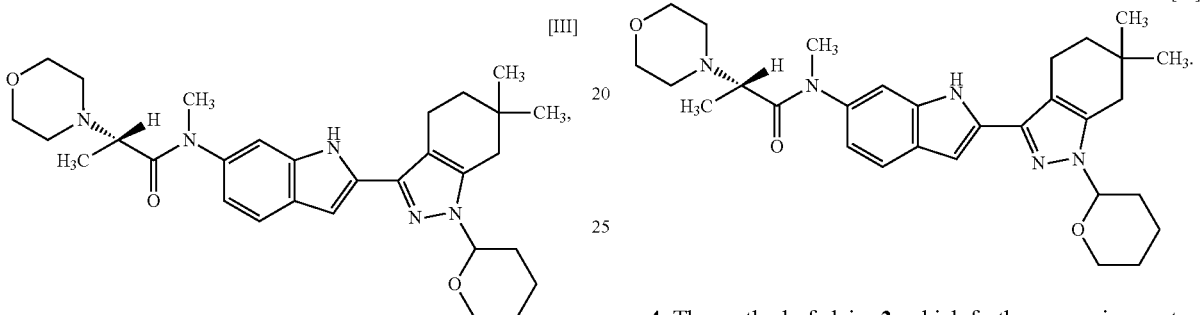

4. The method of claim 3, which further comprises a step of subjecting a compound of the formula [VI]

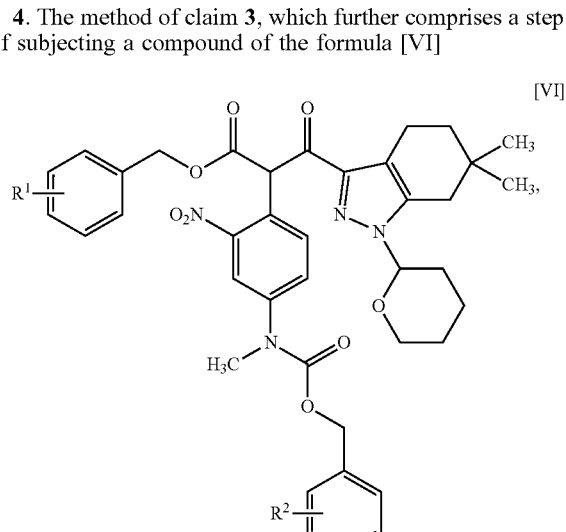

wherein $R^1$ and $R^2$ are each independently hydrogen, $C_{1-6}$ alkyl or $C_{1-6}$ alkoxy, to a reduction reaction to give a compound of the formula [V]

5. The method of claim 4, which further comprises a step of reacting a compound of the formula [VII]

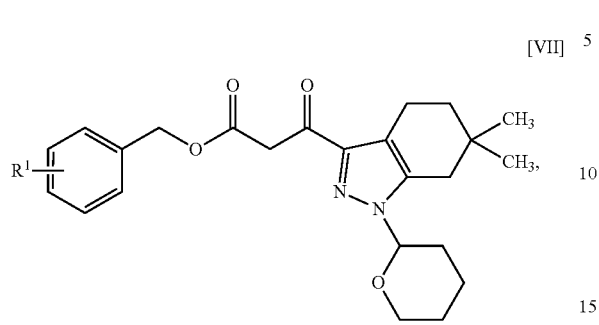

wherein R¹ is as defined in claim 4,
with a compound of the formula [XI]

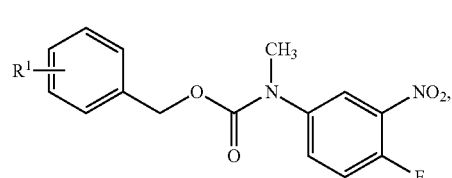

wherein R² is as defined in claim 4,
to give a compound of the formula [VI]

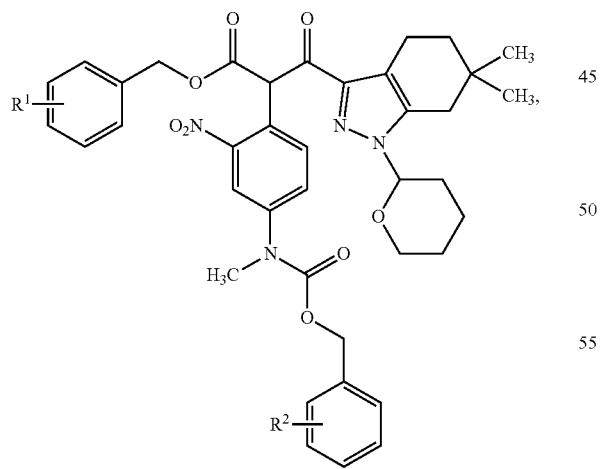

wherein R¹ and R² are as defined above.

6. The method of claim 5, which further comprises a step of subjecting a compound of the formula [VIII]

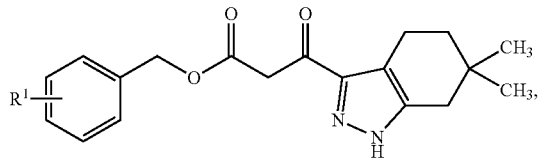

wherein R¹ is as defined in claim 4,
to tetrahydropyranylation to give a compound of the formula [VII]

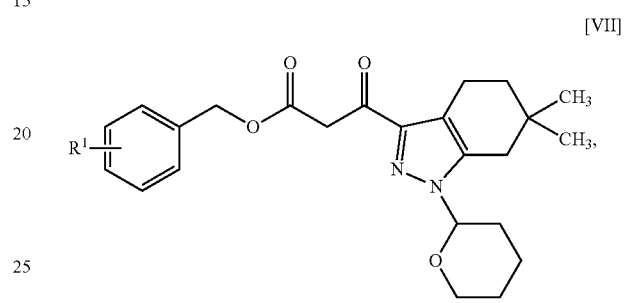

wherein R¹ is as defined above.

7. The method of claim 6, which further comprises a step of reacting a compound of the formula [IX]

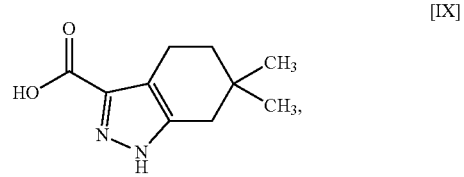

with a compound of the formula [IX]

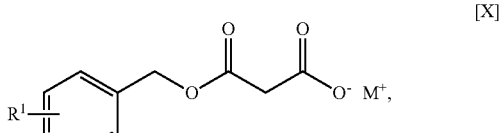

wherein
M is sodium or potassium, and
R¹ is as defined in claim 4,
to give a compound of the formula [VIII]

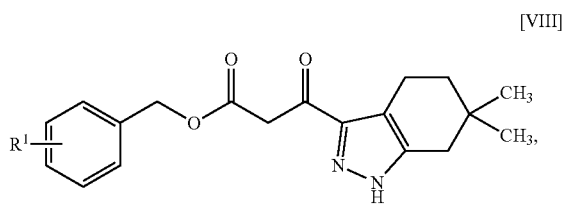

wherein R¹ is as defined above.

8. The method of claim 2, which further comprises a step of purifying a compound of the formula [II]
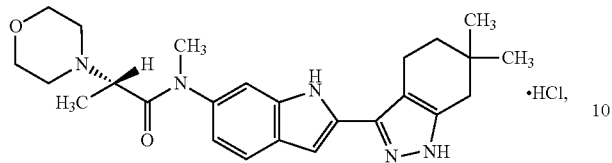
with 1-propanol.

UNITED STATES PATENT AND TRADEMARK OFFICE
CERTIFICATE OF CORRECTION

PATENT NO. : 11,104,667 B2
APPLICATION NO. : 16/263881
DATED : August 31, 2021
INVENTOR(S) : Inoue et al.

Page 1 of 1

It is certified that error appears in the above-identified patent and that said Letters Patent is hereby corrected as shown below:

In the Claims

Column 38, Line 41, Claim 7, "formula [IX]" should read "formula [X]"

Signed and Sealed this
Fourteenth Day of December, 2021

Drew Hirshfeld
*Performing the Functions and Duties of the*
*Under Secretary of Commerce for Intellectual Property and*
*Director of the United States Patent and Trademark Office*